(12) United States Patent
Malik et al.

(10) Patent No.: US 8,597,508 B2
(45) Date of Patent: *Dec. 3, 2013

(54) SOL-GEL MONOLITHIC COLUMN WITH OPTICAL WINDOW AND METHOD OF MAKING

(75) Inventors: Abdul Malik, Tampa, FL (US); James D. Hayes, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/102,651

(22) Filed: May 6, 2011

(65) Prior Publication Data

US 2012/0000850 A1      Jan. 5, 2012

Related U.S. Application Data

(62) Division of application No. 10/203,586, filed as application No. PCT/US01/04271 on Feb. 9, 2001, now Pat. No. 7,947,174.

(60) Provisional application No. 60/181,642, filed on Feb. 10, 2000, provisional application No. 60/181,371, filed on Feb. 9, 2000.

(51) Int. Cl.
*B01D 15/08* (2006.01)

(52) U.S. Cl.
USPC ............. 210/198.2; 210/502.1; 210/635; 210/656

(58) Field of Classification Search
USPC ............ 210/635, 656, 659, 502.1; 204/450, 204/600; 422/70; 436/161, 178
See application file for complete search history.

(56) References Cited

U.S. PATENT DOCUMENTS

| | | | |
|---|---|---|---|
| 4,509,964 A | 4/1985 | Hubball et al. |
| 4,675,300 A | 6/1987 | Zare et al. |
| 4,966,785 A | 10/1990 | Springston |
| 5,128,291 A | 7/1992 | Wax et al. |
| 5,192,406 A | 3/1993 | Woolley |
| 5,240,577 A | 8/1993 | Jorgenson et al. |
| 5,262,052 A | 11/1993 | Rossiter et al. |
| 5,270,027 A | 12/1993 | Balducci et al. |
| 5,308,495 A | 5/1994 | Avnir et al. |
| 5,522,994 A | 6/1996 | Frechet et al. |
| 5,589,396 A | 12/1996 | Frye et al. |
| 5,624,875 A | 4/1997 | Nakanishi et al. |
| 5,637,135 A | 6/1997 | Ottenstein et al. |

(Continued)

FOREIGN PATENT DOCUMENTS

| | | |
|---|---|---|
| WO | WO 00/11463 | 3/2000 |
| WO | WO 02/072225 | 9/2002 |
| WO | WO 02/094410 | 11/2002 |

OTHER PUBLICATIONS

U.S. Appl. No. 10/704,766, filed Nov. 10, 2003, Malik et al.

(Continued)

*Primary Examiner* — Ernest G Therkorn
(74) *Attorney, Agent, or Firm* — Saliwanchik, Lloyd & Eisenschenk

(57) ABSTRACT

A method of preparing a sol-gel monolithic column includes the step of forming a separation bed (14) from a sol-gel solution in a single process step. This column has improved characteristics for CEC based on its incorporated surface charge and ease of operation due to a lack of or need for end frits. Also, a second type of column includes an optical window (30) for on-column detection.

7 Claims, 7 Drawing Sheets

(56) References Cited

U.S. PATENT DOCUMENTS

| | | | |
|---|---|---|---|
| 5,691,206 | A | 11/1997 | Pawliszyn |
| 5,869,152 | A | 2/1999 | Colon |
| 6,136,187 | A | 10/2000 | Zare et al. |
| 6,344,242 | B1 | 2/2002 | Stolk et al. |
| 6,613,234 | B2 | 9/2003 | Voute et al. |
| 6,759,126 | B1 | 7/2004 | Malik et al. |
| 6,783,680 | B2 | 8/2004 | Malik |
| 6,998,040 | B2 | 2/2006 | Malik et al. |
| 2003/0075447 | A1 | 4/2003 | Malik et al. |
| 2004/0129141 | A1 | 7/2004 | Malik et al. |
| 2005/0106068 | A1 | 5/2005 | Malik et al. |
| 2006/0013981 | A1 | 1/2006 | Malik et al. |
| 2006/0013982 | A1 | 1/2006 | Malik et al. |
| 2006/0113231 | A1 | 6/2006 | Malik |
| 2007/0062874 | A1 | 3/2007 | Malik et al. |
| 2007/0095736 | A1 | 5/2007 | Malik et al. |
| 2007/0172960 | A1 | 7/2007 | Malik et al. |

OTHER PUBLICATIONS

Aerts et al., "Preparation, evaluation, and comparison of wide bore (320 μm) and narrow bore (50 μm) cyanosilicone-coated capillary columns for gas chromatography", *Journal of High Resolution Chromatography & Chromatography Communications*, Jan. 1986, vol. 9, pp. 49-56.

Aichholz, R., "Preparation of Glass Capillary Columns Coated with OH-Terminated (3,3,3-Trifluoropropyl) Methyl Polysiloxane (PS 184.5)", *Journal of High Resolution Chromatography*, 13, 71-73 (1990).

ALLTECH, *Chromatography Catalog*, 172 (1997).

Altgelt, K. et al., *Chromatography in Petroleum Analysis*, Marcel Dekker, Inc., New York and Basel (1979).

Albin, M. et al. "Sensitivity Enhancement for Capillary Electrophoresis", *Analytical Chemistry*, 65, 489-497A (1993).

Behnke et al., "Evaluation of the parameters determining the performance of electrochromatography in packed capillary columns," *J. Chromatogr. A.* 716:207-213, 1995.

Behnke et al., "Pressurized gradient electro-high-performance liquid chromatography," *J. Chromatogr A.* 680:93-98, 1994.

Belardi, R. et al., "The Application of Chemically Modified Fused Silica Fibers in the Extraction of Organics from Water Matrix Samples and their Rapid Transfer to Capillary Colums", *Water Pollut. Res. J. Can.*, 24, 179-191 (1989).

Berezkin, V.G. et al., "Capillary Columns with Several Layers of Different Immobilized Stationary Phases", *J. Anal. Chem.—USSR*, 47, 600-604 (1992).

Berezkin, V.G. et al., *Gas Chromatography in Air Pollution Analysis*, Elsevier, Amsterdam—Oxford—New York—Tokyo, Chapter 8, 165-207 (1991).

Bigham, S. et al. "Sol-Gel Capillary Microextraction", *Anal. Chem.* 74, 752-761 (2002).

Blau, K. et al., eds., *Handbook of Derivatives for Chromatography*, 2$^{nd}$ ed., John Wiley & Sons, Chichester—New York—Brisbane—Toronto—Singapore, 1-30 (1993).

Blomberg, L. et al., "Modification of Glass Capillary Columns by Cyclic (3,3,3-Trifluoropropyl)methylsiloxanes", *Journal of HRC & CC*, 3, 527-528 (1980).

Blum, W. "Preparation of inert glass capillary columns coated with ucon 50 hb-5100. An attempt to rediscover industrially produced α, ω-polyethylene/polypropyleneglycol ethers as stationary phases in capillary gas chromatography", *Journal of High Resolution Chromatography & Chromatography Communications*, Jan. 1987, vol. 10, pp. 32-38.

Brinker, C.J. et al., *Sol-Gel Science: The Physics and Chemistry of Sol-Gel Processing*, Academic Press, San Diego—New York—Boston—London—Sydney—Tokyo—Toronto, 97-233 (1990).

Britz-McKibbin, P. et al. "Selective Focusing of Catecholamines and Weakly Acidic Compounds by Capillary Electrophoresis Using Dynamic pH Junction", *Anal. Chem.*, 72, 1242-1252 (2000).

Britz-McKibbin, P. et al. "On-Line Focusing of Flaving Derivative Using Dynamic pH Junction-Sweeping Capillary Electrophoresis with Laser-Induced Fluorescence Detection", *Anal. Chem.*, 3736-3743 (2002).

Brown, P. B et al "The Separation and the Characterization of Long Chain Fatty Acids and Their Derivatives by Reversed Phase High Performance Liquid Chromatography", *Analytical Chemistry*, 21, 193-208, (1989).

Cao, C. -X. et al. "Stacking Ionizable Analytes in a Sample Matrix with High Salt by a Transient Moving Chemical Reaction Boundary Method in Capillary Zone Electrophoresis", *Anal. Chem.* 74, 4167-4174 (2002).

Chen, Z. et al. "Chemically Modified chiral monolithic Silica Column Prepared by a Sol-Gel Process for Enantiomeric Separation by Micro High-Performanc Liquid Chromatography", *J. Chromatogra.*, 942, 83-91 (2002).

Chien, R.-L. et al. "Sample Stacking of an Extremely Large Injection Volume in High-Performance Capillary Electrophoresis", *Anal. Chem.*, 64, 1046-1050 (1992).

Chien, R.-L. et al. "On-Column Sample Concentration Using Field Amplification in CZE", *Anal. Chem.*, 64, 489A-496A (1992).

Chong et al. "Sol-Gel Coating Technology for the Preparation of Solid-Phase Microextraction Fibers of Enhanced Thermal Stability" *Analytical Chemistry* 1997, 69, 3889-3898.

Chun, M.-S. et al. "Protein Analysis with Large Volume Sample Stacking with an Electrosmotic Flow Pump: A Potential Approach for Proteomics", *Microchem. J.*, 70, 247-253 (2001).

Church, M. N. et al. "Transient Isotachophoretic-Electrophoretic Separations of Lanthanides with Indirect Laser-Induced Fluorescence Detection", *Anal. Chem.*, 70, 2475-2480 (1998).

Cifuentes, A. et al. "Capillary Isoelectric Focusing of Erythropoietin Giycoforrns and its Comparison with Flat-bed Isoelectric Focusing and Capillary Zone Electrophoresis", *J. Chromatogra.*, 830, 453-463 (1999).

Clarke, N. J. et al. "Capillary Isoelectric Focusing-Mass Spectrometry: Analysis of Protein Mixtures from Human Body Fluids", *Biomed. Chromatogr.*, 16, 287-297 (2002).

Clifford, A. A. "Introduction to Supercritical Fluid Extraction in Analytical Science", in *Supercritical Fluid Extraction and its Use in Chromatographic Sample Preparation*, Westwood, S. A. (ed.), 1-38 (1993).

Collinson, M. M. et al. "Sol-gels and Electochemistry", *Analytical Chemistry*, 72, 702A-709A (2000).

Colon et al., "Ninth International Symposium on High Performance Capillary Electrophoresis and Related Microscale Techniques." (HPCE '97). Anaheim, California 1997. Abstract.

Cortes, H.J. et al., "Porous Ceramic Bed Supports for Fused Silica Packed Capillary Columns Used in Liquid Chromatography", *J. High Resolut. Chromatogr. and Chromatogr. Commun.*, 1987, 10, 446-448.

Coulibaly, K. et al. "An overview of Solid-Phase Extraction of Food Flavor Compounds and Chemical Residues", *Food Rev. Int.*, 12, 131-151 (1996).

Deng, Y. et al. "Chip-Based Quantitative Capillary Electrophoresis/ Mass Spectrometry Determination of Drugs in Human Plasma", *Anal. Chem.*, 73, 1432-1439 (2001).

Dittmann et al., "Capillary electrochromatography—a high-efficiency micro-separation technique," *J. Chromatogr. A*. 744:63-74, 1996.

Dulay, M.T. et al., "Preparation and Characterization of Monolithic Porous Capillary Columns Loaded with Chromatographic Particles", *Anal. Chem.*, 1998, 70(23), 5103-5107.

Ericson et al., "Preparation of continuous beds for electrochromatography and reversed-phase liquid chromatography of low-molecular-mass compounds," *J. Chromatogr. A*. 767:33-41, 1997.

Ericson et al., "Reversed-Phase Electrochromatography of Proteins on Modified Continuous Beds Using Normal-Flow and Counterflow Gradients. Theoretical and Practical Considerations," *Anal. Chem.* 71: 1621-1627. 1999.

Ettre, L.S., "Performance of Open Tubular Columns as a Function of Tube Diameter and Liquid Phase Film Thickness", *Chromatographia*, 18, 477-488 (1984).

(56) References Cited

OTHER PUBLICATIONS

Ettre, L.S. et al., *Basic Relationships of Gas Chromatography*, Advanstar, Cleveland, OH, 1-34 (1993).

Farbrot et al., "polymerized stationary phases in 12 to 50 µm open tubular fused silica columns for LC and GC", *Journal of High Resolution Chromatography & Chromatography Communications*, Feb. 1986, vol. 9, pp. 117-119.

Ferioli, V. et al., "High-Performance Liquid Chromatography of Dihydroxyacetone as its bis-2,4-Dinitrophenylhydrazone Derivative," *Chromatographia*, 41, 61-65 (1995).

Fields, S.N., "Silica Xerogel as a Continuous Column Support for High-Performance Liquid Chromatography", *Anal. Chem.*, 1996, 68, 2709-2712.

Frame et al., "Simplification of capillary electrochromatography procedure's," *J. Chromatogr. A*. 798:243-249, 1998.

Furton, K. G. et al. "The Use of Solid-Phase Microextraction-Gas Chromatography in Forensic Analysis", *Journal of Chromatographic Science*, 38, 297-306, (2000).

Fujimoto et al., "Charged Polyacrylamide Gels for Capillary Electrochromatographic Separations of Uncharged, Low Molecular Weight Compounds," *Anal. Chem.* 67:2050-2053, 1995.

Fujimoto et al., "Fritless Packed Columns for Capillary Electrochromatography: Separation of Uncharged Compounds on Hydrophobic Hydrogels," *Anal. Chem.* 68:2753-2757, 1996.

Guo, Y. et al. "A Stationary Phase for Open Tubular Liquid Chromatography and Electrochromatography Using Sol-Gel Technology", *Anal. Chem.*, 67, 2511-2516 (1995).

Hamlet, C. et al., "Novel Sol-Gel Dendrimer Coatings for Ultra-Trace Environmental Analysis by Capillary Microextraction Coupled to Gas Chromatography", *5th International Symposium on Advances in Extraction Technologies*, St. Pete Beach, FL (Mar. 5-7, 2003).

Hartmann, H. et al., "Trace Determination of Pesticides in Water by Coated Capillary Micro Extraction (CCME) and Reversed-Phase High Performance Liquid Chromatography", *Fresenius Environmental Bulletin*, 7, 96-103 (1998).

Haruvy, Y. et al., "Sol-Gel Replication of Microoptical Elements and Arrays", *Chem. Mater.*, 9, 2604-2615 (1997).

Hayes, J. D. et al. "Sol-Gel Process Mediated Advanced Column Technology for Microcolumn Separations", *18th International Symposium on Capillary Chromatogr.*, 1, 496-504 (1996).

Hayes, J.D. et al., "Sol-Gel Monolithic Columns with Reversed Electroosmotic Flow for Capillary Electrochromatography", *Anal. Chem.*, 72, 4090-4099 (2000).

Hayes, J.D. et al., "Sol-Gel Open Tubular ODS Columns with Reversed Electroosmotic Flow for Capillary Electrochromatography", *Anal. Chem.*, 73, 987-996 (2001).

Hayes, J.D. et al., "Sol-Gel Chemistry-Based Ucon-coated Columns for Capillary Electrophoresis", *J. Chromatogr. B*, 695, 3-13 (1997).

Hetem et al., "Deactivation with polymethylhydrosiloxane: A comparative study with capillary gas chromatography and solid-state $^{29}$Si nuclear magnetic resonance spectroscopy", *Journal of Chromatography*, Aug. 1989, vol. 477, No. 1, pp. 3-24.

Hileman et al., "In Situ Preparation and Evaluation of Open Pore Polyurethane Chromatographic Columns," *Anal. Chem.* 45:1126-1130, 1973.

Hiraoka, A. et al. "One-Step Capillary Isoelectric Focusing of th Proteins in Cerebrospinal Fluid and Serum of Patients with Neurological Disorders", *J. Chromatogr. A*, 961, 147-153 (2002).

Hjerten et al., "Continuous beds: high-resolving, cost-effective chromatographic matrices," *Nature* 356:810-811, 1992.

Hjerten et al., "High-performance liquid chromatography on continuous polymer beds," *J. Chromatogr.* 473:273-275, 1989.

Hjertén, S. et al. "Adaptation of the Equipment for High-Performance Electrophoresis to Isoelectric Focusing", *J. Chromatogr.*, 346, 265-270 (1985).

Huang, M. et al. "Charged Surface Coatings for Capillary Electrophoresis", *J. Microcol.*, 5, 199-205 (1993).

Ishizuka et al., "Designing monolithic double-pore silica for high-speed liquid chromatography," *J. Chromatogr. A*. 797:133-137,1998.

Janák, K. et al., "Static Coating of Capillary Columns by Means of Liquefied Gases", *Journal of High Resolution Chromatography & Chromatography Communications*, 8, 843-847 (1985).

Jorgenson et al., "High-Resolution Separations Based on Electrophoresis and Electroosmosis," *J. Chromatogr A*. 218:209-216, 1981.

Kameoka, J. et al. "A Polymeric Microfluidic Chip for CE/MS Determination of Small Molecules", *Anal. Chem.*, 73, 1935-1941 (2001).

Kataoka, H. et al., "Automated In-Tube Solid-Phase Microextraction Coupled with Liquid Chromatography/Electrospray Ionization Mass Spectrometry for the Determination of β-Blockers and Metabolites in Urine and Serum Samples", *Anal. Chem*, 71, 4237-4244 (1999).

Kataoka, H. et al. "Simple and Rapid Determination of Amphetamine, Methamphetamine, and Their Methylenedioxy Derivatives in Urine by Automated In-Tube Solid-Phase Microextraction Coupled with Liquid Chromatograpy-Electrospray Ionization Mass Spectrometry", *Journal of Analytical Toxicology*, 24, 257-265 (2000).

Kim, J-B. et al. "On-line Sample Concentration in Micellar Electrokinetic Chromatography Using Cationic Surfactants", *J. Chromatogr. A*, 916, 123-130 (2001).

Knox et al., "Miniaturisation in Pressure and Electroendosmotically Driven Liquid Chromatography: Some Theoretical Considerations," *Chrornatographia* 24: 135-143, 1987.

Koivusalmi, E. et al., "Quantitative RP-HPLC Determination of Some Aldehydes and Hydroxyaldehydes as Their 2,4-Dinitrophenylhydrazone Derivatives". *Anal. Chem.*, 71, 86-91 (1999).

Lee, M. L. et al. "Fused Silica Capillary Column Technology for Gas Chromatography", *J. Chromatog. Sci.*, 22, 136-142 (1984).

Li et al., "Continuous Beds for Microchromatography: Cation-Exchange Chromatography," *Anal. Biochem*. 223:153-158, 1994.

Lichtenberg, J. et al. "Sample Preconcentration by Field Amplification Stacking for Microchip-Based Capillary Electrophoresis", *Electrophoresis*, 22, 258-271 (2001).

Liu, Q. et al. "Poly(diallyldirnethylammonium chloride) as a Cationic Coating for Capillary Electrophoresis", *J. Chromatogr. Sci.*, 36, 126-130 (1997).

Locke, S. et al. "Techniques for the Optimization of Proteomic Strategies Based on Head Coumn Stacking Capillary Electrophoresis", *Anal. Chem.*, 72, 2684-2689 (2000).

Lopez-Avila, V. et al. "Evaluation of Soxtec Extraction Procedure for Extracting Organic Compounds from Soils and Sediments", *J. AOAC International*, 76, 864-880 (1993).

Ludtke et al., "Application of 0.5- µm porous silanized silica beads in electrochromatography," *J. Chromatogr. A*. 786:229-235, 1997.

MacKenzie, J. D. et al. "Hybrid Organic-Inorganic Materials, The Sol-Gel Approach" in *ACS Symposium Series*, 585, 226-236 (1995).

Majors, R. E. "Liquid Extraction Techniques for Sample Preparation", *LC GC International*, 10, 93-101 (1997).

Malik, A. et al., "Advanced Sol-gel Column Technology for Condensed-phase Microseparations", 25 Proc. *19th International Symposium on Capillary Chromatography and Electrophoresis*, Wintergreen, VA, USA, 54-55 (May 18-22, 1997).

Malik, A. and Chong, S. In Pawliszyn. J. (ed.), "Sol-Gel Technology for Thermally Stable Coatings in SPME, Applications of Solid Phase Microextraction", Royal Society of Chemistry, 1999, United Kingdom, Ch. 6, pp. 73-91.

Markides, K. E. et al. "Deactivation of Fused Silica Capillary Columns with Phenylhydrosiloxanes", *J. High Res. Chromatography & Chromatography Comm.*, 8, 378-384 (1985).

Martin, A. J. P. et al. "Displacement Electrophoresis", *Proc. Roy. Soc, Lond. A.*, 316, 493-514 (1970).

Minnich, M. M. et al. "Extraction Methods for Recovery of Volatile Organic Compounds from Fortified Dry Soils", *J. AOAC International*, 79, 1198-1204 (1996).

Merriam-Webster's Collegiate Dictionary, 10th edition, Merriam-Webster, Incorporated, Springfield Massachusetts, 1998, p. 555.

Minakuchi et al., "Effect of domain size on the performance of octadecylsilylated continuous porous silica columns in reversed-phase liquid chromatography," *J. Chromatogr. A*. 797:121-131, 1998.

Moffat et al., "Capillary Electrochromatography. Abnormally High Efficiencies for Neutral-Anionic Compounds under Reversed-Phase Conditions." *Anal. Chem.* 71:1119-1124, 1999.

(56) References Cited

OTHER PUBLICATIONS

Mukherjee, S.P., "Supercritical Drying in Structural and Microstructural Evolution of Gels: A Critical Review", *Ultrastructure Processing of Advanced Ceramics*, J.D. MacKenzie and D.R. Ulrich, eds., John Wiley & Sons, New York—Chichester—Brisbane—Toronto—Singapore, 747-758 (1988).

Nakanishi et al., "Double Pore Silica Gel Monolith Applied to Liquid Chromatography," *J. Sol-Gel Sci. and Tech.* 8:547-558, 1997.

Nawrocki, J. "Silica Surface Controversies, Strong Adsorption Sites Their Blockage and Removal. Part I", *Chromatographia*, 31, 177-205 (1991).

Novak, B. M. "Hybrid Nanocomposite Materials—Between Inorganic Glasses and Organic Polymers", *Advanced Materials*, 5, 422-433 (1993).

Núñez, O. et al. "Sample Stacking with Matrix Removal for the Determination of Paraquat, Diquat and Difenzoquat in Water by Capillary Electrophoresis", *J. Chromatogr. A*, 912, 353-361 (2001).

Oesterhelt, G. et al., "Analyse von Hydroxypivalaldehyd als Trimethylsilylderivat des Oxims mittels Gas-Chromatographic", *Fresenius Z. Anal. Chem.*, 321, Abstract (1985).

Ogden, M. W. et al. "Characterization of Fused-Silica Capillary Tubing by Contact Angle Measurements", *J. Chromatogr.*, 354, 7-18 (1986).

Palkar, V.R., "Sol-Gel Derived Nanostructured γ-Alumina Porous Spheres as an Adsorbent in Liquid Chromatography", *NanoStructured Materials*, 11, 369-374 (1999).

Pawliszyn, J., "Theory of Solid-Phase Microextraction," *Journal of Chromatographic Science*, 38, 270-278 (1999).

Palm et al., "Macroporous Polyacrylamide/Poly(ethylene glycol) Matrixes as Stationary Phases in Capillary Electrochromatography," *Anal. Chem.* 69:4499-4507, 1997.

Palmer, J. et al. "Stacking Neutral Analytes in Capillary Electrokinetic Chromatographic with High-Salt Sample Matrixes", *Anal. Chem.*, 72, 1941-1943 (2000).

Palmer, J. et al. "A Universal Concept for Stacking Neutral Analytes in Micellar Capillary Electrophoresis", *Anal. Chem.*, 71, 1679-1687 (1999).

Palmer, J. et al. "Electrokinetic Injection for Stacking Neutral Analytes in Capillary and Microchip Electrophoresis", *Anal. Chem.*, 73, 725-731 (2001).

Peters et al., "Molded Rigid Polymer Monoliths as Separation Media for Capillary Electrochromatography," *Anal. Chem.* 69:3646-3649, 1997.

Peters et al., "Molded Rigid Polymer Monoliths as Separation Media for Capillary Electrochromatography. 1. Fine Control of Porous Properties and Surface Chemistry," *Anal. Chem.* 70:2288-2295, 1998.

Pietrzyk et al., "Ion Exchangers," Packings and Stationary Phases in Chromatographic Techniques; Unger, K.K., vol. 47. Marcel Dekker, Inc.: New York and Basel, 1990, Chapter 10.

Pretorius et al., "Electro-Osmosis A New Concept for High-Speed Liquid Chromatography," *J. Chromatogr.* 99:23-30, 1974.

Quirino, J. P. et al. "Approaching a Million-Fold Sensitivity Increase in Capillary Electrophoresis with Direct Ultraviolet Detection: Cation-Selective Exhaustive Injection and Sweeping", *Anal. Chem.* 72, 1023-1030 (2000).

Quirino, J. P. et al. "Sweeping of Analyte Zones in Electrokinetic Chromotography", *Anal. Chem.* 71, 1638-1644 (1999).

Quirino, J. P. et al. "Exceeding 5000-Fold Concentration of Dilute Analytes in Micellar Electrokinetic Chromatography", *Science*, 282, 465-468 (1998).

Quirino, J. P. et al. "On-line Concentration of Neutral Analytes for Micellar Electrokinetic Chromatography II. Reversed Electrode Polarity Stacking Mode", *J. Chromatogr. A*, 791, 255-267 (1997).

Quirino, J. P. et al. "Sweeping with an Enhanced Electric Field of Neutral Analyte Zones in Electrokinetic Chromotography", *J. High Resol. Chromatogr.*, 22, 367-372 (1999).

Quirino, J. P. et al. "On-line Concentration of Neutral Analytes for Micellar electrokinetic Chromatography 5. Field-Enhanced Sample Injection with Reversed Migrating Micelles," *Anal. Chem*, 70, 1893-1901 (1998).

Quirino, J. P. et al. "On-line Concentration of Neutral Analytes for Micellar Electrokinetic Chromatography I. Normal Stacking Mode", *J. Chromatogr. A*, 781, 119-128 (1997).

Reighard, T. S. et al. "Bridging the Gap Between Supercritical Fluid Extraction and Liquid Extraction Techniques: Alternative Approaches to the Extraction of Solid and Liquid Environmental Matrices", *Critical Reviews in Analytical Chemistry*, 26(2&3), 61-99, (1996).

Righetti, P. G. et al. "Study of haptoglobin-hemoglobin Complexes by Titration Curves, Capillary Electrophoresis and Capillary Isoelectric Focusing", *J. Chromatogr. A*, 767, 255-262 (1997).

Röder et al., "Chiral SFC-separations using polymer-coated open tubular fused silica columns. comparison of enantiomeric selectivity in SFC and LC using the same stationary phase of the pirkle type", *Journal of High Resolution Chromatography & Chromatography Communications*, Dec. 1987, vol. 10, pp. 665-667.

Rosenfeld, J. "Gas Chromatography Profiling in Biomedical Investigations" in *Chemical Analysis: Gas Chromatography*, Clement, R. E. (ed.), 111, 181-215 (1990).

Rotzsche, H. "Chemically Bonded Stationary Phases", in Stationary Phases in Gas Chromatography, *Journal of Chromatography Library*, vol. 48, 142-159, (1991), Elsevier.

Schomburg, G. et al. "Alkylpolysiloxane Glass Capillary Columns Combining High Temperature Stability of the Stationary Liquid and Deactivation of the Surface; Thermal Treatment of Dealkalinized Glass Surfaces by the Stationary Liquid Itself", *Chromatographia*, 12(10), 651-660, (1979).

Schutjes, C. P. M. et al. "Deactivation and Coating of Non-Polar 50 μm I.D. Capillary Columns", *J. Chromatogr.*, 279, 49-57 (1983).

Seifar et al., "Capillary electrochromatography with 1.8- μm ODS-modified porous silica particles," *J. Chromatogr. A*. 808:71-77, 1998.

Shen, Y. et al. "High-Efficiency Capillary Isoelectric Focusing of Peptides", *Anal. Chem.*, 72, 2154-2159, (2002).

Shende, C. et al. "Sol-Gel Poly(ethylene Glycol) Stationary Phase for High-Resolution Capillary Gas Chromatography", *Anal. Chem.*, 75, 3518-3530 (2003).

Shihabi, Z. K. "Stacking in Capillary Zone Electrophoresis", *J. Chromatogr. A.*, 902, 107-117 (2000).

Shihabi, Z. K. "Stacking and Discontinuous Buffers in Capillary Zone Electrophoresis", *Electrophoresis*, 21, 2872-2878 (2000).

Shihabi, Z. K. "Transient Pseudo-Isotachophoresis for Sample Concentration in Capillary Electrophoresis", *Electrophoresis*, 23, 1612-1617 (2002).

Shihabi, Z. K. et al. "Insulin Stacking in Capillary Zone Electrophoresis", *J. Chromatogr. A.*, 807, 129-133 (1998).

Smith et al., "Capillary zone electrophoresis in pharmaceutical and biomedical analysis," *Journal of Pharmaceutical & Biomedical Analysis* 12:579-611, 1994.

Soderquist, A. Office Action mailed Jul. 2, 2003 in U.S. Appl. No. 09/763,419.

Soderquist, A. Office Action mailed Jan. 5, 2004 in U.S. Appl. No. 09/763,419.

Soderquist, A. Office Action mailed May 26, 2004 in U.S. Appl. No. 09/763,419.

Soderquist, A. Office Action mailed Feb. 11, 2005 in U.S. Appl. No. 09/763,419.

Soderquist, A. Office Action mailed Sep. 20, 2005 in U.S. Appl. No. 09/763,419.

Spanik, I. et al. "Use of Full-Column Imaging Capillary Isoelectric Focusing for the Rapid Determination of the Operating Conditions in the Preparitive-Scale Continuous Free Flow Isoelectric Focusing Separation of Enantiomers", *J. Chromatogr. A.*, 960, 241-246 (2002).

Stark, F. O. et al. "The Interactions between Trialkylsilanes and E-Glass or Aerosil Surfaces. Reactions of Trimethylsilanol, Trimethylchlorosilane, and Hexamethyldisilazane", *The Journal of Physical Chemistry*, 72(8), 2750-2754, (1968).

Strausbauch, M. A. et al. "Mechanism of Peptide Separation by Solid Phase Extraction Capillary Electrophoresis at Low pH", *Anal. Chem.*, 68, 306-314 (1996).

(56) References Cited

OTHER PUBLICATIONS

Steenackers et al., "Capillary GC on micrometer i.d. columns coated with thick films. theory and selected practical results", *Journal of High Resolution Chromatography*, Feb. 1995, vol. 18, pp. 77-82.

Sumpter, S.R. et al. "Static Coating of 5 to 50 μm I.D. Capillary Columns for open Tubular Column Chromatography", *J. Chromatogr.*, 517, 503-519 (1990).

Sun, P. et al. "Chitosan Coated Capillary with Reserved Electroosmotic Flow in Capillary Electrophoresis for the Separation of Basic Drugs and Proteins", *J. Microcol*, Sep. 6, 403-407 (1994).

Svec et al., "Continuous Rods of Macroporous Polymer as High-Performance Liquid Chromatography Separation Media," *Anal. Chem.* 64:820-822, 1992.

Svec et al., "Modified poly(glycidyl methacrylate-co-ethylene dimethacrylate) continuous rod columns for preparative-scale ion-exchange chromatography of proteins," *J. Chromatogr. A*. 702:89-95, 1995.

Tang et al., "Continuous Bed Columns Containing Sol-Gel Bonded Large-Pore Octadecylsilica for Capillary Electrochromatography," *J. Microcol.* Sep. 11:550-561, 1999.

Toussaint, B. et al. "Enantiomeric Separation of Clenbuterol by transient Isotachophoresis-capillary zone Electophoresis-UV Detection New Optimization Technique for Transient Isotachophoresis", *J. Chromotogr. A*. 173-180 (2000).

Traitler, "A cold silanization method for preparation of medium polarity capillary columns" *Journal of High Resolution Chromatography & Chromatography Communications*, Feb. 1983, vol. 6, pp. 60-63.

Tsuda, T., "Electrochromatography Using High Applied Voltage," *Anal. Chem*, 59:521-523, 1987.

Tu, C. et al. "Determination of Nitrate in Seawater by Capillary Zone Electophoresis with Chloride-Induced Sample Self-Stacking", *J. Chromatogr. A.*, 966, 205-212 (2002).

Van Den Bosch, "Experiences with packed capillary electrochromatography at ambient pressure;" *J. Chromatogr. A.* 755:165-177,1996.

Van Der Vlis, E. et al. "Combined liquid-liquid electroextraction and isotachophoresis as a fast on-line focusing step in capillary electrophoresis", *Journal of Chromatography A*, 687, 333-341, (1994).

Veraart, J. B. et al. "At-Line Solid-Phase Extraction Coupled to Capillary Electrophoresis: Determination of Amphoteric Compounds in Biological Samples", *J. High Resol. Chromatogr.*, 22, 183-187 (1999).

Vorotilov, K. A. et al. "ORMOSIL Films: Properties and Microelectronic Applications" *Journal of Sol-Gel Science and Technology*, 8, 581-584, (1997).

Wang et al., "Macroporous Polymeric Stationary-Phase Rod as Continuous Separation Medium for Reversed-Phase Chromatography," *Anal. Chem.* 65:2243-2248, 1993.

Wang, D. et al. "Preparation and GC Performance of Sol-Gel Technology-Based Open Tubular Columns" *Eighteenth International Symposium on Capillary Chromatography*, vol. I, May 20-24, 1996, pp. 505-513.

Wang, D. et al., "Sol-Gel Column Technology for Single-Step Deactivation, Coating, and Stationary-Phase Immobilization in High-Resolution Capillary Gas Chromatography", *Anal. Chem.*, 69, 4566-4576 (1997).

Wang, Z. et al. "High-performance polyethylene glycol-coated solid-phase microextraction fibers using sol-gel technology" *Journal of Chromatography A*, 893, 157-168, (2000).

Wei, W. et al. "One-Step Concentration of Analytes Based on Dynamic Change in pH in Capillary Zone Electrophoresis", *Anal. Chem.*, 74, 934-940 (2002).

Welsch, T. et al. "The Thermal Immobilization of Hydroxy-Terminated Silicone Phases in High-Temperature-Silylated Glass Capillaries. A Study of Reaction Mechanisms", *Journal of High Resolution Chromatography*, 14, 153-159, (1991).

Wercinski, S.A.S. et al. "Solid Phase Microextraction Theory" in *Solid Phase Microextraction, a Practical Guide*, 1999, 1-26, Marcel Dekker, Inc., New York.

Wilkes, G. L. et al. "'Ceramers'; Hybrid Materials Incorporating Polymeric/Oligomeric Species into Inorganic Glasses Utilizing a Sol-Gel Approach", *Polymer Preprints* 26(2), 300-302 (1985).

Woolley, C. L. et al. "Deactivation of Fused Silica Capillary Columns with Polymethylhydrosiloxanes", *J. High Resol. Chromatogr./Chromatogr. Comm.*, 7, 329-332 (1984).

Wu, J. et al. "Polypyrrole-Coated Capillary Coupled to HPLC for In-Tube Solid-Phase Microextraction and Analysis of Aromatic Compounds in Aqueous Samples", *Anal. Chem.*, 73, 55-63, (2001).

Wu, J. et al. "Polypyrrole-Coated Capillary In-Tube Solid Phase Microextraction Coupled with Liquid Chromatography-Electrospray Ionization Mass Spectrometry for the Determination of 62 -Blockers in Urine and Serum Samples", *J. Microcolumn Separations*, 12(4), 255-266, (2000).

Wu, J. et al. "Speciation of Organoarsenic Compounds by Polypyrrole-Coated Capillary In-Tube Solid Phase Microextraction Coupled With Liquid Chromatograph/Electrospray Ionization Mass Spectrometry", *Analytica Chimica Acta*, 424, 211-222 (2000).

Yakabe, Y. et al. "Immobilization Method for Polyethylene Glycol Using a Cross-linking Co-agent", *J. Chromatogr.*, 558, 323-327 (1991).

Zapf, A. et al. "GC Analysis of Organic Acids and Phenols Using On-Line Methylation with Trimethylsulfonium Hydroxide and PTV Solvent Split Large Volume Injection", *J. High Resol. Chromotogr.*, 22, 83-88 (1999).

Zeng, Z. et al. "Solid-Phase Microextraction Using Fused-Silica Fibers Coated with Sol-Gel-Derived Hydroxy-Crown Ether", *Anal. Chem.*, 73, 2429-2436 (2001).

Zhang, J. et al. "Development of the Personal Aldehydes and Ketones Sampler Based upon DNSH Derivatization on Solid Sorbent", *Environ. Sci. Technol.*, 34, 2601-2607 (2000).

Zhang, Y. et al. "High Performance Micellar Liquid Chromatography with Silica Microparticles Having Surface-bound Cationic Surfactant Moieties. I. Comparison with Octadecylsilica and Applications to the Separation of Dansyl Amino Acids, Herbicides, and Catecholamines", *Journal of Liquid Chromatography*, 18(17), 3373-3396 (1995).

Zhang, Z. et al. "Solid-Phase Microextraction", *Anal. Chem.* 66, 844A-853A (1994).

Nawrocki, J. "How strongly do silanols interact with hydrocarbon solutes in gas chromatography?" *J. Chrom.*, 1986, 362:117-120.

Kohler, J. and Kirkland, J.J. "Improved silica-based column packings for high-performance liquid chromatography" *J. Chrom.*, 1987, 385:125-150.

Kominar, R.J. "The preparation and testing of a fused-silica gas chromatography capillary column" *J. Chem. Edu.*, 1991, 68:A249-A255.

Kohr, J. and Engelhardt, H. "Characterization of quartz capillaries for capillary electrophoresis" *J. Chrom. A*, 1993, 652:309-316.

Gilges, M. et al. "Capillary zone electrophoresis separations of basic and acidic proteins using poly(vinyl alcohol) coatings in fused silica capillaries" *Anal. Chem.*, 1994, 66:2038-2046.

Denton, K.A. and Harris, R. "High-performance capillary electrophoretic separation of human serum albumin using a neutral coated capillary" *J. Chrom. A*, 1995, 704:335-341.

Capelli, L. et al. "Tunable positive negative surface charges on a capillary wall: exploiting the immobiline chemistry" *J. Biochem. Biophys. Methods*, 1996, 32:109-124.

Huang, X. et al. "Spectroscopic probing of mixed-mode adsorption of Ru(bpy)3 2+ to silica" *Anal. Chem.*, 1996, 68:4119-4123.

Lipkowitz, K.B. et al. "Explanation of where and how enantioselective binding takes place on permethylated β-cyclodextrin, a chiral stationary phase used in gas chromatography" *J. Am. Chem. Soc.*, 1997, 119:600-610.

Jennings, W. et al. "The Open Tubular Column" in Analytical Gas Chromatography, 1997, pp. 30-48, Academic Press, San Diego, CA.

Horvath, J. and Dolnik, V. "Polymer wall coatings for capillary electrophoresis" *Electrophoresis*, 2001, 22:644-655.

(56) References Cited

OTHER PUBLICATIONS

Moseley, M.A. and Pellizzari, E.D. "Polysiloxane deactivated fused silica capillaries containing immobilized stationary phases" *J. of HRC & CC*, 1982, 5:472-475.

Ogden, M.W. and McNair, H.M. "Hydrothermal treatment of fused silica capillary columns" *J. of HRC & CC*, 1985, 8:326-331.

Faramawy, S. et al. "Surface-modified silica gels as solid stationary phases in gas chromatography" *Surface and Coatings Tech.*, 1997, 90:53-63.

Nawrocki, J. "The silanol group and its role in liquid chromatography" *J. Chrom. A*, 1997, 779:29-71.

Horka, M. et al. "Influence of the capillary dimensions on the performance of the preconcentration technique based on parallel current chromatography" *J. Chrom. A*, 1997, 791:163-176.

US 8,597,508 B2

SOL-GEL MONOLITHIC COLUMN WITH OPTICAL WINDOW AND METHOD OF MAKING

CROSS-REFERENCE TO RELATED APPLICATIONS

The present application is a divisional of U.S. application Ser. No. 10/203,586, filed Oct. 16, 2002, now U.S. Pat. No. 7,947,174, which is the National Stage of International Application Number PCT/US01/04271, filed Feb. 9, 2001, which claims the benefit of U.S. Application Ser. No. 60/181,642, filed Feb. 10, 2000 and U.S. Application Ser. No. 60/181,371, filed Feb. 9, 2000, all of which are incorporated herein by reference.

BACKGROUND OF THE INVENTION

1. Field of the Invention

The present invention relates to columns and methods of making columns for separation techniques and apparatus. More specifically, the present invention provides a separation bed and method of making the same for use in various electromigration and non-electromigration separation columns, such as high-performance liquid chromatography, gas chromatography, capillary electrophoresis, capillary electrochromatography, and supercritical fluid chromatography.

2. Description of Related Art

Capillary electrochromatography or CEC is a fairly novel electrokinetic separation technique representing a hybrid of high-performance liquid chromatography or HPLC and capillary electrophoresis, known as CE. In CEC, the electroosmotic flow, or EOF is used to drive the mobile phase through the capillary, using typical HPLC mobile and stationary phases that provide the essential chromatographic interactions. Because of the flat plug-like profile of the electroosmotic flow, CEC offers greatly enhanced separation efficiencies relative to HPLC. Unlike CE, CEC is not restricted to charged solutes. Thus, the potential for CEC, as a separation technique, is much wider.

Capillary electrochromatography is a rapidly growing area in analytical separations. A great deal of research effort is currently being devoted to materialize the great analytical potential that this new hybrid technique has to offer. In order for CEC to achieve success as an independent chromatographic separation technique significant advancements are needed in the area of column technology. This is explained by the fact that in CEC, the column not only serves as the separation chamber, but also as the pumping device to drive the mobile phase through the system. This makes the column the "heart" of the CEC system both in the functional and literal sense of the word.

Two major types of columns are used in current CEC practice. These are packed and open tubular types. Packed columns comprise the predominant class of CEC columns. Most often the packed capillaries contain 1.5-5 μm, non-polar, octadecylated or ODS particles. The ODS particles possess both the chemically bonded octadecyl stationary phase, providing the essential chromatographic interactions, and the silanol moieties, responsible for the generation of electroosmotic flow to drive the mobile phase and the solutes through the packed capillary. The commercial availability of the ODS-bonded particles and the previously established liquid chromatography or LC separation protocols are two advantages attracting many researchers to use these packed capillaries in CEC. However, the most significant advantage of packed columns in CEC is the possibility of using small micrometer and nanometer size particles. High separation efficiency during fast analysis is achieved in packed CEC columns without requiring ultra-high pressures, as in HPLC to drive the mobile phase through the columns packed with the small particles.

The greatest challenge is the preparation of a uniform packing bed using the small particles. Researchers currently use a variety of packing procedures ranging from slurry packing, electrokinetic, centripetal, and supercritical fluid packing methods. These all involve a plurality of steps to effect the packing process and even with close monitoring do not give as uniform a bed as desired for many applications.

Furthermore, a great degree of difficulty still remains associated with the ability to pack long, narrow bore capillaries. In addition, most packed capillaries require end flits of a different material to retain the packing particles within the packed capillary bed. Creation of those flits remains to be a problem in column preparation as these flits must be rigid enough to retain the packing particles under a wide range of column packing, rinsing and operating conditions. Yet these flits must also possess a highly porous structure to permit a uniform mobile phase flow through the entire cross-section of the column. A further problem arises in that the presence of the frit material makes the packing in the column non-homogeneous due to the presence of a different material and this can cause problems with the separation characteristics of the final column.

Monolithic column technology can effectively overcome both of the difficulties associated with conventional packed capillary column technology. In the monolithic approach, a continuous separation bed is created inside the capillary tube using a solution, which undergoes both chemical and physical changes in the capillary environment to produce the separation bed. In addition, the choice of appropriate chemistry allows the porous bed to chemically bond to the inner walls of the capillary by a condensation reaction and the resulting packed tube is also homogeneous in nature.

The use of monolithic columns has been reported in gas and liquid chromatography and is also currently being used in CEC to alleviate the extensive labor involved with packed column fabrication. Moreover, the greatest inherent advantage of the monolithic capillary columns is the elimination of the need for the end frits. The elimination of these end frits allows the entire column to remain homogeneous, rather than exhibiting different properties by the packing particles and the end frits. It has also been demonstrated that the end frits reduce the column's separation efficiency and are responsible for bubble formation during the analysis.

Although much simpler than particle packed capillaries, monolithic columns derived by organic polymerization also possess certain limitations. One critical drawback associated with this type of monolithic capillary is the tendency of the polymer network to swell during exposure to certain organic solvents, which are contained in the running mobile phase. This swelling may result in reductions in the permeability of the monolith as a result of alterations in the porosity of the monolith. Such structural change ultimately leads to changes in the column performance during the course of its use.

Unlike the monolithic separation beds from organic polymers, columns-containing a porous silica-based monolithic matrix prepared through sol-gel chemistry do not suffer from the swelling phenomena thus offering a versatile and promising alternative to organic packed capillaries. In addition, monolithic columns, since they are prepared without end frits can produce a homogeneous separation column, which is highly desirable for a wide variety of separation techniques.

Pretorius was one of the first influential pioneers of CEC who, in 1974, demonstrated the advantages of electroosmosis as a pumping mechanism for chromatographic separations. Jorgenson and Lukacs published CEC analyses of 9-methylanthracene and perylene on an ODS-packed capillary column. Meanwhile, a 1987 report by Tsuda demonstrated the possibility of achieving CEC separations by the simultaneous use of both electroosmotic and pressure-driven flows in the separation column. Yet Knox and Grant made another significant contribution to the development of this technique. Following this publication, the term "electrochromatography" became generally accepted and numerous researchers refocused their attention to CEC.

As described earlier, two types of monolithic columns have been developed: (1) organic polymer-based and (2) bonded silica-based. In the first approach, fabrication of a monolithic capillary column is accomplished by polymerization reaction of organic monomeric precursor(s). Hileman et al used Carbowax coated open pore polyurethane monolithic capillaries for the separations of several classes of analytes including aromatic hydrocarbons, aliphatic alcohols and metal chelates through gas chromatography. Hjerten et al prepared monolithic capillaries with compressed polyacrylamide gels for separation of proteins using HPLC and of low molecular mass compounds and basic proteins using CEC. Frechet and coworkers reported a series of publications on the use of methacrylate monomers for the preparation of HPLC and CEC monolithic capillaries through copolymerization. Palm and Novotny prepared CEC monoliths using mixtures of polyacrylamide/polyethylene glycol, derived with either $C_4$ or $C_{12}$ ligands, which were used to separate alkyl phenones and peptides. Additionally, Fujimoto et al reported the usage of cross-linked polyacrylamides for the separation of small dansylated amino acids and neutral steroids on monolithic CEC capillaries.

An alternative to a column with an organic polymer-based stationary phase column is one with a bonded silica stationary phase prepared by sol-gel chemistry. Cortes and coworkers prepared porous beds by polymerizing potassium silicate solutions in situ. The columns containing the porous beds were then packed with 5 μm Spherisorb ODS particles for use in LC. Fields used solutions of potassium silicate and formamide to create a porous bed that was further reacted with dimethyloctadecylchlorosilane, and achieved plate heights of 65 μm in LC.

Tanaka and coworkers used the sol-gel technique for the development of an octadecylsilylated, porous monolithic column for use in LC. In this study, poly(ethylene oxide), PEO, was incorporated into a mixture of tetramethoxysilane (TMOS) and acetic acid to develop porous silica rods, followed by an in-column octadecylsilylation reaction. Following washings, and drying at 50° C. for three days, the silica rods were then treated for two hours at 600° C.

Dulay et al used sol-gel technology for the preparation of monolithic columns loaded with 3 μm ODS particles. The sol-gel solution served as a retaining matrix immobilizing and shielding the ODS stationary phase particles. Sol-gel capillary columns containing the ODS embedded particles yielded CEC separation efficiencies on the order of 80,000 plates/m (16,000 plates/column) for a test mixture of six uncharged polyaromatic hydrocarbons or PAHs.

Lee and coworkers also used sol-gel chemistry to glue 7 μm ODS particles thereby creating a continuous large-pore CEC column. The sol-gel technology in this approach was used to create a bridge between adjacent particles; as well as the capillary wall and particles in its vicinity, thereby eliminating the need for retaining end-frits, thus result being efficient separations of small organic and aromatic amine compounds on such "sol-gel-glued" monolithic columns.

SUMMARY OF THE INVENTION

It is, therefore, an object of the invention to create a monolithic column from a sol-gel process.

It is also an object of the invention to prepare a sol-gel column having a porous, separation bed without the use of particles being incorporated into the bed.

It is a further object of the invention to create a sol-gel column in a single-step process that obviates the need for a plurality of processing steps.

It is another object of the invention to produce a monolithic sol-gel column, which is chemically bonded to the capillary wall.

It is a further object of the invention to produce a monolithic sol-gel column that does not require high temperature processing steps.

It is another object of the invention to produce a monolithic sol-gel column having an optical window useful for on-column detection studies of the analytes separated by the separation column, using various spectral techniques.

BRIEF DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE PREFERRED EMBODIMENTS

Figure 1:
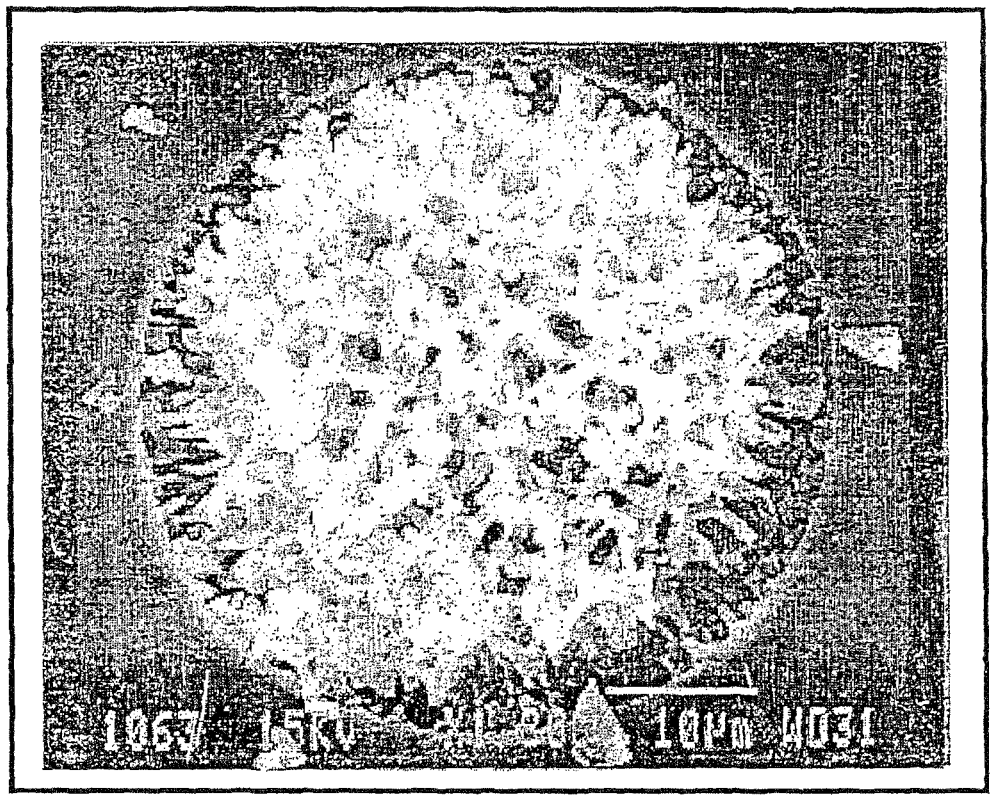
FIG. 1 is a scanning electron micrograph of a sol-gel monolithic column, cross-sectional view, magnified 1,800 times.

In the present invention, monolithic sol-gel columns are prepared by an in situ creation of chromatographic stationary phases with surface-bonded ligands. Unlike conventional techniques, various column preparation processes, such as deactivation, coating/packing, stationary-phase immobilization and end frit making, are carried out in one single step, thus reducing the time and labor associated with column fabrication. In addition, the process produces a column that is homogenous since there are no particles included in the sol-gel and the sol-gel monolithic bed actually forms bonds with the fused silica capillary surface, making a unitary structure across the diameter of the tube.

In order to achieve the desired sol-gels of the instant invention, certain reagents in a reagent system were preferred for the fabrication of the gels for the monolithic columns of the present invention. The reagent system included two sol-gel precursors, a deactivation reagent, one or more solvents and a catalyst. For the purposes of this invention, one of the sol-gel precursors contains a chromatographically active moiety selected from the group consisting of octadecyl, octyl, cyanopropyl, diol, biphenyl, phenyl, cyclodextrins, crown ethers and other moieties. Representative precursors include, but are not limited to: Tetramethoxysilane, 3-(N-styrlmethyl-2-aminoethylamino)-propyltrimethoxysilane hydrochloride, N-tetradecyldimethyl(3-trimethoxysilylpropyl)ammonium chloride, N(3-trimethoxysilylpropyl)-N-methyl-N,N-diallylammonium chloride, N-trimethoxysilylpropyltri-N-butylammonium bromide, N-trimethoxysilylpropyl-N,N,N-trimethylammonium chloride, Trimethoxysilylpropylthiouronium chloride, 3-[2-N-benzyaminoethylaminopropyl]trimethoxysilane hydrochloride, 1,4-Bis(hydroxydimethylsilyl)benzene, Bis(2-hydroxyethyl)-3-aminopropyltriethoxysilane, 1,4-bis(trimethoxylylethyl)benzene, 2-Cyanoethyltrimethoxysilane, 2-Cyanoethyltriethoxysilane, (Cyanomethylphenethyl) trimethoxysilane, (Cyanomethylphenethyl)triethoxysilane, 3-Cyanopropyldimethylmethoxysilane, 3-Cyanopropyltriethoxysilane, 3-Cyanopropyltrimethoxysilane, n-Octadecyltrimethoxysilane, n-Octadecyldimethylmethoxysilane, Methyl-n-Octadecyldiethoxysilane, Methyl-n-Octadecyldimethoxysilane, n-Octadecyltriethoxysilane, n-Dodecyltriethoxysilane, n-Dodecyltrimethoxysilane, Octyltriethyoxysilane, n-Octyltrimethoxysilane, n-Ocyldiisobutylmethoxysilane, n-Octylmethyldimethoxysilane, n-Hexyltriethoxysilane, n-isobutyltriethoxysilane, n-Propyltrimethoxysilane, Phenethyltrimethoxysilane, N-Phenylaminopropyltrimethoxysilane, Styrylethyltrimethoxysilane, 3-(2,2,6,6-tetramethylpiperidine-4-oxy)-propyltriethoxysilane, N-(3-triethoxysilylpropyl)acetyl-glycinamide, (3,3,3-trifluoropropyl)trimethoxysilane, and (3,3,3-trifluoropropyl)methyldimethoxysilane.

A second sol-gel precursor, N-Octadecyldimethyl[3-(trimethoxysilyl)propyl]ammonium chloride, was found to be critical since it possessed an octadecyl moiety that allowed for chromatographic interactions of analytes with the monolithic stationary phase. Additionally, this reagent served to yield a positively charged surface thereby providing the relatively high electroosmotic flow necessary in capillary electrochromatography. However, it is considered within the scope to use any other reagent as known to one of ordinary skill in the art that would contain the octadecyl moiety for the purposes already set forth.

The deactivation reagent, Phenyldimethylsilane, and the catalyst, Trifluoracetic acid, were selected for the preparation of the columns of the instant invention, however, any know deactivation reagent and/or catalyst as known to those of ordinary skill in the art may be used.

The sol-gel solutions were prepared by mixing 100 µL of Tetramethyloxysilane (TMOS) with 100 µL of $C_{18}$-TMS (N-Octyldecyl-dimethyl[3-(trimethoxy-silyl)propyl]ammonium chloride), 10 µL of PheDMS (Phenyldimethylsilane), 100 µL of 99% Trifluoroacetic acid (TFA) (containing 10% water), and 100 µL of 90% TFA (containing 10% water) in a micro vial. This mixture was thoroughly vortexed for 5 minutes, and the precipitate was then separated from the sol-gel solution through centrifugation at 13,000 rpm for 5 minutes. The supernatant was decanted into another micro vial and used for the creation of the monolithic separation bed.

A standard fused silica capillary tube, as known to those of skill in the art, was selected to be filled with the sol-gel solution. The tube used here was externally coated with polyimide, however it is within the scope of the invention to use a tube coated with any polymer or other coating such as metal, as known in the art; the external coating serving as a structural integrity device for the tube.

Prior to filling with the sol-gel solution, the inner surface of the capillary was first treated with deionized water. For this, an approximately 5 meter long section of 50 µm internal diameter fused silica capillary was rinsed with deionized water for approximately 15 minutes under a helium pressure of 200 psi. The capillary was then emptied by expelling the water from within by using the same helium pressure. Both ends of the capillary tube were then fused using an oxyacetylene torch, and the capillary was placed in a GC oven for thermal conditioning by raising the temperature at 0.5° C./min from 40° C. to a final temperature of 250° C. with a hold time of 60 minutes at 250° C. The column was then removed from the GC oven, and the ends were opened, followed by purging of the column with helium under 200 psi pressure for an additional 30 minutes.

Next, a desired length, for example 60 cm, of the hydrothermally pretreated fused-silica capillary was taken and installed into the capillary filling chamber, containing a polyethylene microcentrifuge vial with the desired sol-gel solution. It is, of course, within the scope of the invention to use any desired length as desired by one of skill in the art. Using 100 psi helium pressure, the sol solution was pushed into the column. The column, containing the sol solution, was then allowed to remain installed in the pressurized capillary chamber and left undisturbed for approximately four hours until gelation of the sol solution was visually apparent. Following this, the pressure was slowly released and the column was removed from the capillary filling/purging chamber. It was then affixed perpendicular to the bench top. A 60-s epoxy seal was then applied to the ends of the capillary to ensure adequate sealing prior to its thermal conditioning. Next, a very slow thermal conditioning program was used. An example of this thermal conditioning consists of a programmed temperature heating at 0.2° C./min from 35° C. (1 minute hold time) to a final temperature of 150° C., where the column has held for 120 minutes. Following heating, the ends were cut open and the monolithic capillary was then installed into a Bio-Rad CE system for subsequent rinsing at 100 psi. It is, of course, contemplated that any CE system as known to those of skill in the art may also be used. The monolithic column was initially rinsed with 100% HPLC grade acetonitrile, followed by a 50:50 acetonitrile/deionized water solution for periods of 5 minutes each, and finally the desired running mobile phase for 15 minutes prior to conducting column evaluation and/or analysis.

Visualization of the monolithic microstructure within the capillary tube was accomplished through the use of a scanning electron microscope. All scanning electron micrographic images were acquired from sections of the monolithic column initially cut into equal lengths, those being approximately 2.5 mm, and positioned perpendicularly within a retractable aluminum stage using a double-sided tape. These samples were then used to obtain cross-sectional views of the monolithic CEC columns. Longitudinal sections were acquired by dissecting approximately 1.0 cm sections of capillary at approximately 45°, thus yielding a capillary segment revealing a protruding portion of the monolithic matrix without the top portion of the fused silica present. These sections were then mounted parallel on an aluminum stage with the aid of double-sided carbon tape. Both stages, with all mounted capillary segments, were then consecutively placed into a Balzers SCD 050 sputter coating chamber and coated with a gold/palladium alloy at 40 mA for 60 seconds to avert subsequent charging.

Figure 2:
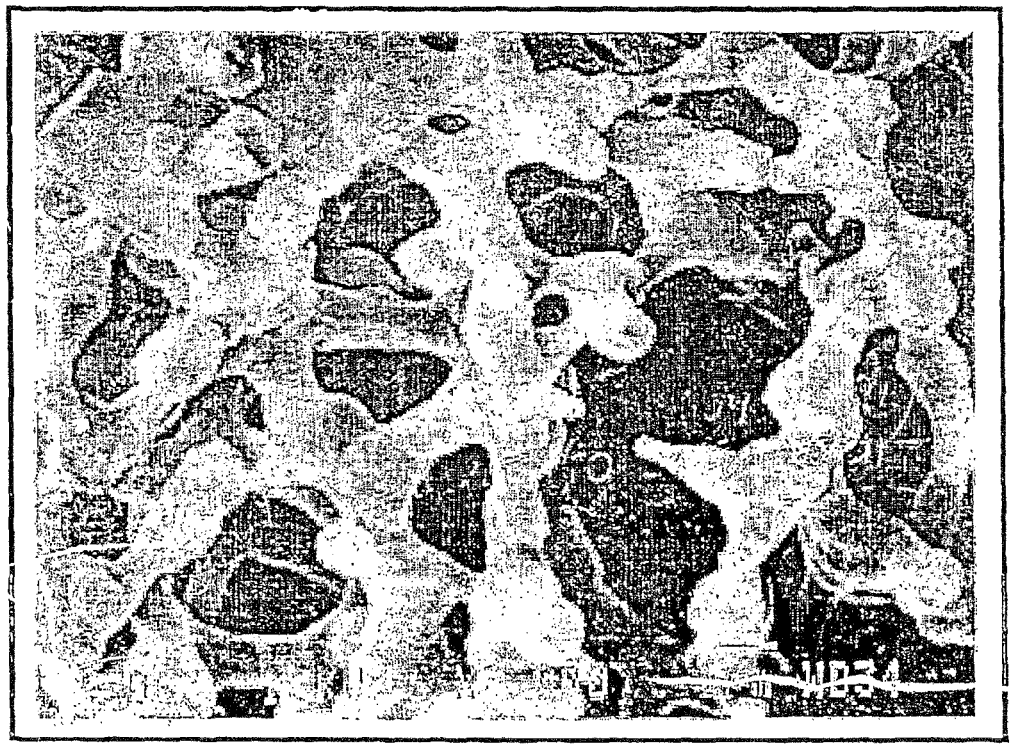
FIG. 2 is a scanning electron micrograph of a sol-gel monolithic column, longitudinal view, magnified 7,000 times.

FIG. 1 represents a SEM cross-sectional view of the sol-gel monolithic column at a magnification of 1800×. Observations at this magnification reveal that the entire cross-section of the capillary contains the monolithic matrix. FIG. 2, a longitudinal view of the monolithic capillary at 7000× magnification, reveals the porous structure of the monolithic matrix. From this view it is evident that the pore diameters are of approximately 1.5 μm. The use of higher $C_{18}$TMS-to-TMOS molar ratios in the sol solution provided monolithic beds with the said pore characteristics. This also allowed for enhanced permeability of the mobile phase.

For example, an increase in the $C_{18}$TMS-to-TMOS molar ratio of from 0.5 to 0.75 yielded flow rates of up to approximately 7.75 μL/min for the mobile phase consisting of 80% (v/v) Acrylonitrile 20% (v/v)/5 mM Tris-HCl. Dimethylsulfoxide (DMSO) was used as the neutral EOF marker to determine the linear velocity of the mobile phase and was found to be 0.97 mm/s using the mobile phase.

Figure 3:
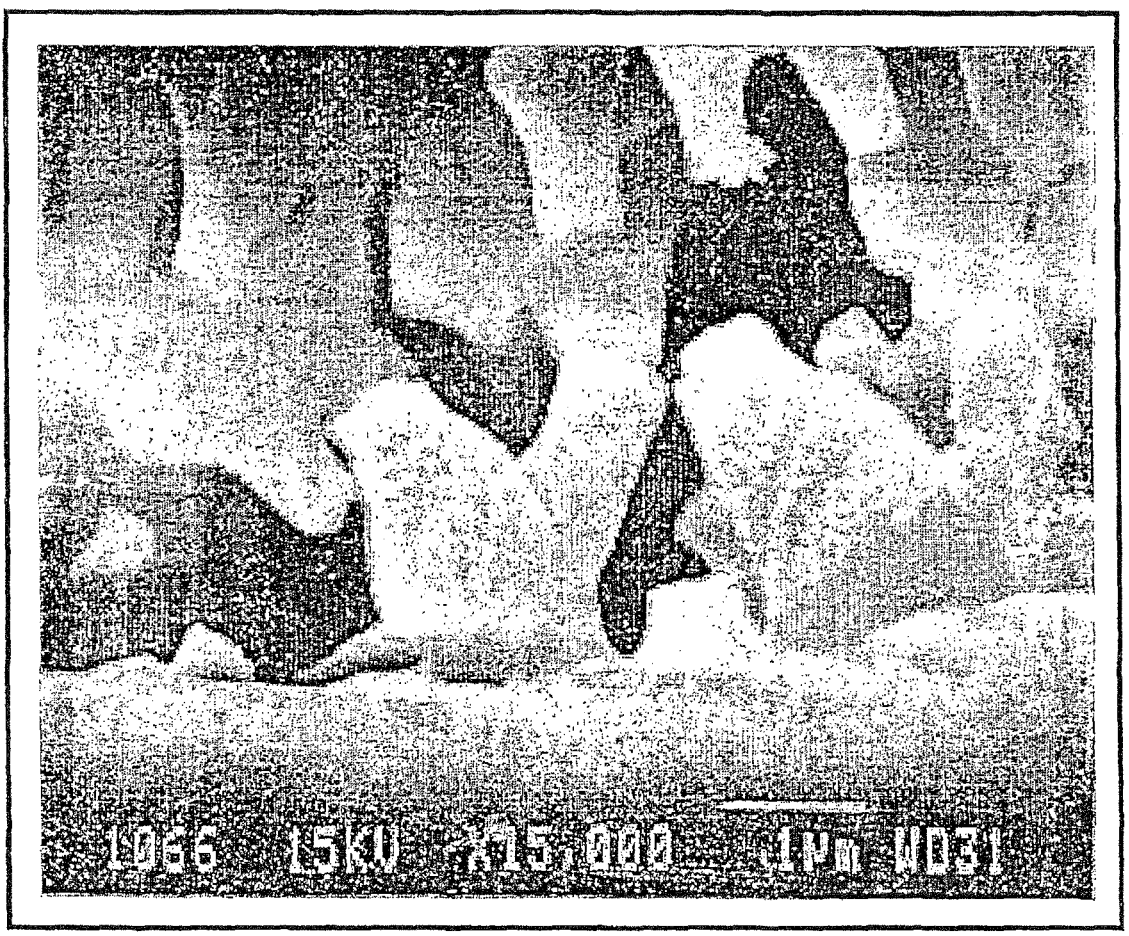
FIG. 3 is a scanning electron micrograph of a sol-gel monolithic column, longitudinal view, magnified 15,000 times.

FIG. 3, a cross-sectional view of the inner capillary at higher magnification (15000×), reveals the chemical bonding during the column preparation process that occurred due to the condensation between the sol-gel network structure and the silanol moieties on the inner capillary walls.

The scanning electron micrograph studies show that sol-gel chemistry provides a unique, yet simple mechanism for the fabrication of CEC monolithic columns. One of the key sol-gel reactions consists of the hydrolysis of the precursors. This is shown below with respect to the use of TMOS and $C_{18}$TMS. It is understood that this choice of reagents is for illustrative purposes only and others can be used as described before:

The Complete Hydrolysis of N-Octadecyldimethyl [3-(thimethyloxysilyl)propyl] ammonium chloride $C_{18}$—TMS (a) and tetramethoxysilane (TMOS) (b) (a)

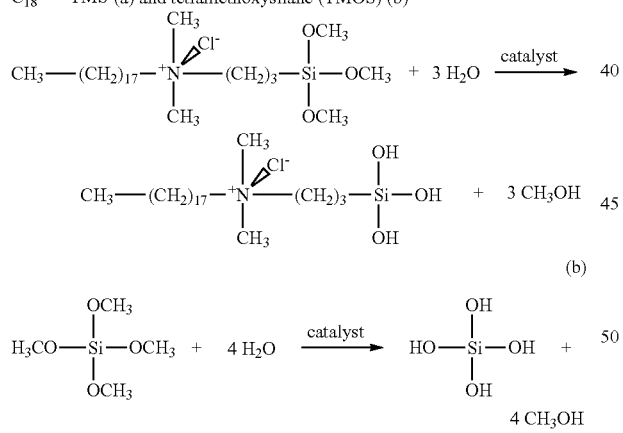

As shown above, the nucleophilic attack of water molecules on the silicon atom results in the replacement of the methoxy substituents with hydroxy moieties. As the sol-gel reactions proceed, the products of the hydrolysis can then undergo polycondensation reactions in a variety of ways: (a) between hydrolyzed products of the same original precursor, (b) between hydrolyzed products of two different original precursors, and (c) between the hydrolysis products of either precursor with the silanol groups on the inner capillary surface. A simplified representation of a polycondensation reaction between the hydrolysis products of both precursors is depicted below:

Condensation of Tetrahydroxysilane with N-Octadecyldimethyl[3-(trihydroxysilyl)propyl] ammonium chloride

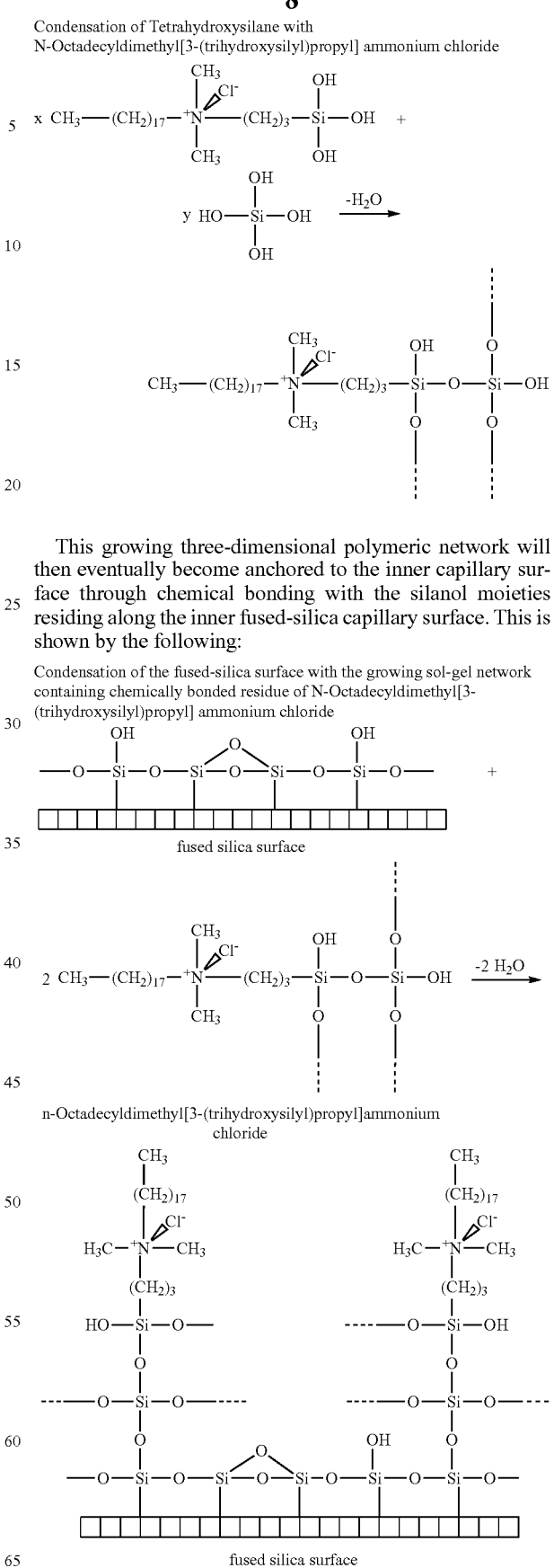

This growing three-dimensional polymeric network will then eventually become anchored to the inner capillary surface through chemical bonding with the silanol moieties residing along the inner fused-silica capillary surface. This is shown by the following:

Condensation of the fused-silica surface with the growing sol-gel network containing chemically bonded residue of N-Octadecyldimethyl[3-(trihydroxysilyl)propyl] ammonium chloride Finally, the incorporation of the PheDMS into the sol solution serves as a deactivating reagent for the monolithic bed. This deactivation reagent is initially added to the sol solution. The mobile hydrogen bonded to silicon atom in the structure of this reagent is reactive toward silanol groups, especially at elevated temperatures. It can be assumed that during the sol-gel process, this reagent becomes physically incorporated in the monolithic structure but subsequently, during thermal treatment of the column, reacts with the residual silanol groups in the monolithic structure providing deactivation, as shown below:

and usage. Thorough degassing of the mobile phase was necessary to prevent subsequent bubble formation/generation during usage. This initial degassing procedure allowed for electrochromatographic experiments to be continuously performed without pressurization of the mobile phase. To achieve the desired concentration of aqueous electrolyte, a 50 mM solution was initially prepared followed by dilution to achieve the 5 mM concentration. The pH of this 5 mM solution was then measured and adjusted to approximately 2.3 by using concentrated HCl. This 5 mM Tris-HCl, having a pH of approximately 2.3 solution, in conjunction with 100% aceto-

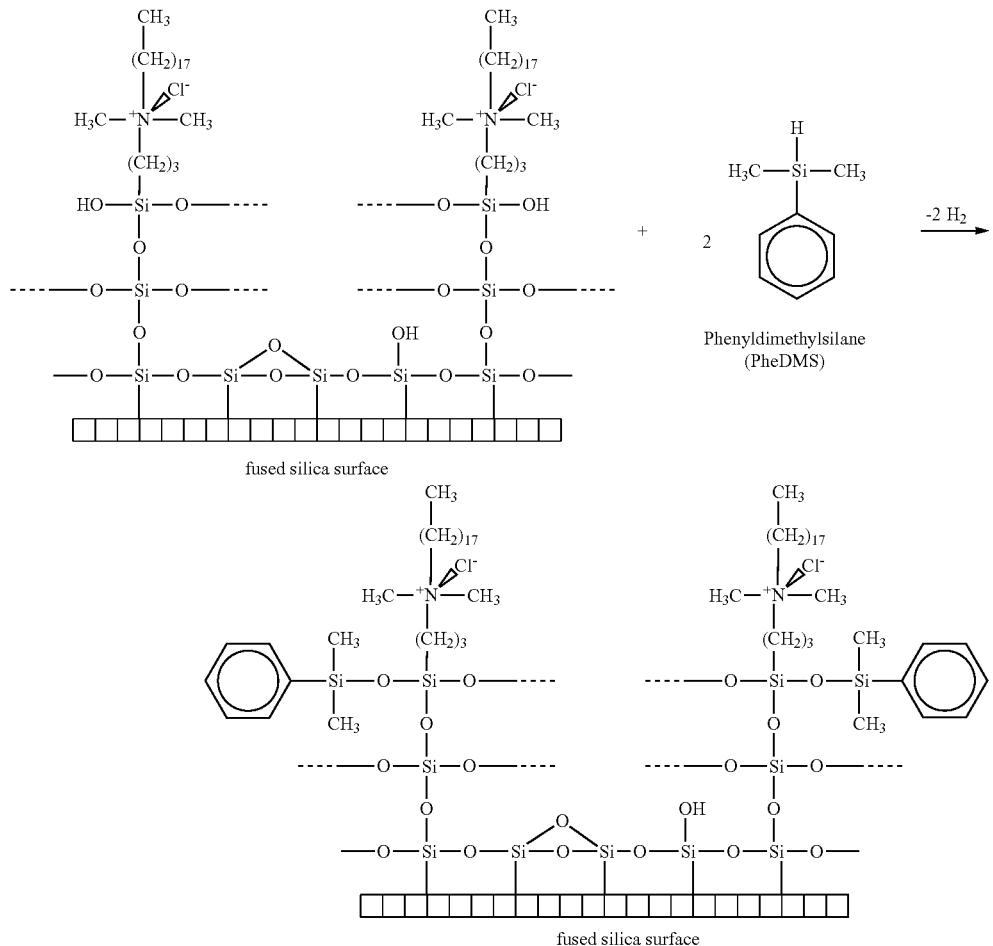

Thus it has been shown that the sol-gel process provides a chemical anchorage of the monolithic matrix to the inner walls of the capillary (FIG. 3). This thoroughly illustrates a significant attribute of the sol-gel monolithic column. Another aspect is that the sol-gel monolithic bed is completely held in the column chemical bonding with the walls of the capillary, thus obviating the need for any end frits to hold the column material in place within the capillary.

Several analyses were performed using the monolithic columns of the instant invention. Each mobile phase was prepared by mixing the desired volumes of acetonitrile with a Tris-HCl background electrolyte solution. The organic solvent and the background electrolyte solution were thoroughly degassed individually via simultaneous ultrasonication and helium purging for approximately one hour prior to mixing nitrile was individually degassed by simultaneous ultrasonication and helium purging, followed by mixing the solution in appropriate volume ratios (e.g., 75% acetonitrile/25% 5 mM Tris-HCl, etc.) to prepare the running mobile phase.

Figure 4:
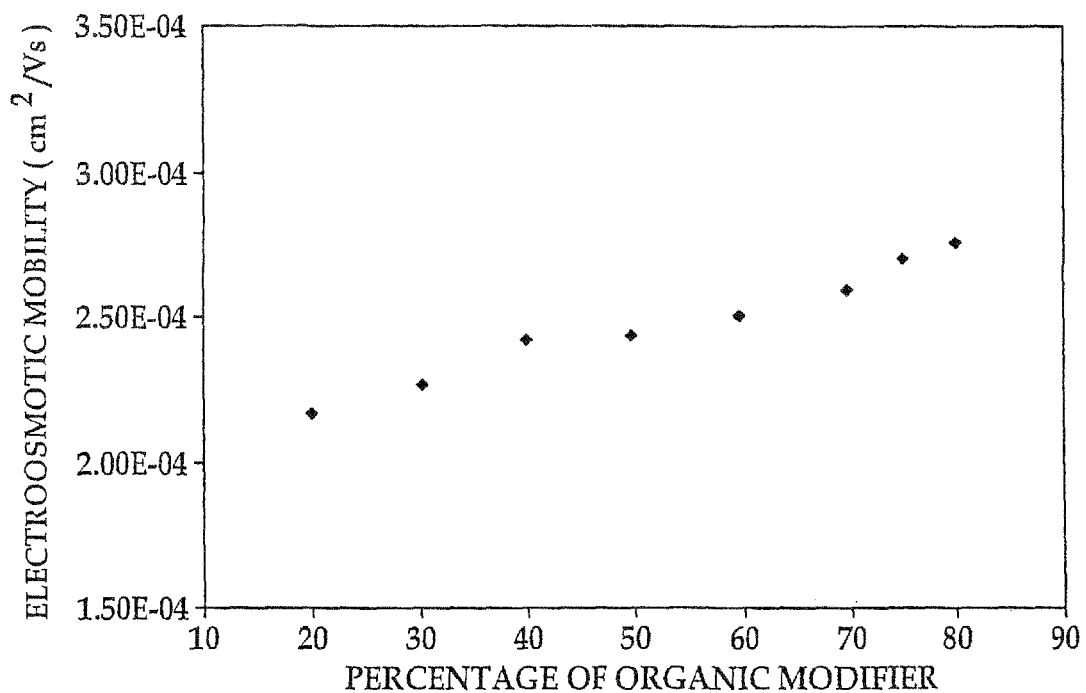
FIG. 4 is a graph of the effect of the change of electroosmotic mobility with an increase in percentage of acetonitrile and Tris-HCl in a mobile phase.

Experiments were conducted for the investigation of the electroosmotic flow (EOF) in sol-gel monolithic columns. The first measurements obtained using the monolithic ODS capillary was an evaluation of the effect of acetonitrile percentage in the running mobile phase on the electroosmotic mobility. For this, a set of mobile phases containing varying percentages of acetonitrile and 5 mM aqueous Tris-HCl was utilized. In addition, DMSO was used as the neutral electroosmotic flow marker. The results obtained from these experiments are depicted in FIG. 4. As illustrated, the electroosmotic mobility within the ODS monolithic capillary consistently increased with the acetonitrile content in the mobile phase. Such an increase in EOF is indicative of an increase in the net positive surface charge within the monolithic columns. One possibility for this to occur is the reduction of effective negative surface charge due to an increase in acetonitrile concentration in the mobile phase, resulting in an equivalent increase of the effective positive surface charge due to the quaternary ammonium groups. This is possible because the negative charge on the monolith/capillary is reduced due to the interaction of acetonitrile with the negative-charge generating surface groups such as the silanols.

In CEC, a consistent EOF is essential to drive the analyte(s) through the separation column. This EOF is generated due to an electrical double layer at the interface of the solid support with the liquid mobile phase. Most commonly, silica is used as the solid support and develops a negative surface charge under CE/CEC running conditions, presumably as a result of the deprotonation of the silanol groups. The negatively charged substrate attracts cations from the electrolyte in the mobile phase thereby forming the electrical double layer.

In this invention, the positively charged quaternary ammonium moiety contained in the N-octadecyldimethyl[3-(trimethoxysilyl)propyl]ammonium chloride provided a positively charged surface on the monolithic matrix, which, in turn, counteracted on the effects of the residual silanol groups residing both on the monolith and on the inner capillary surface. Under the experimental conditions used, a strong EOF was observed in the reversed direction (from cathode to anode), suggesting that the surface positive charge due to quaternary ammonium functionality in the surface-bonded $C_{18}TMS$ moieties is the EOF-determining factor in the prepared sol-gel monolithic columns.

Figure 5:
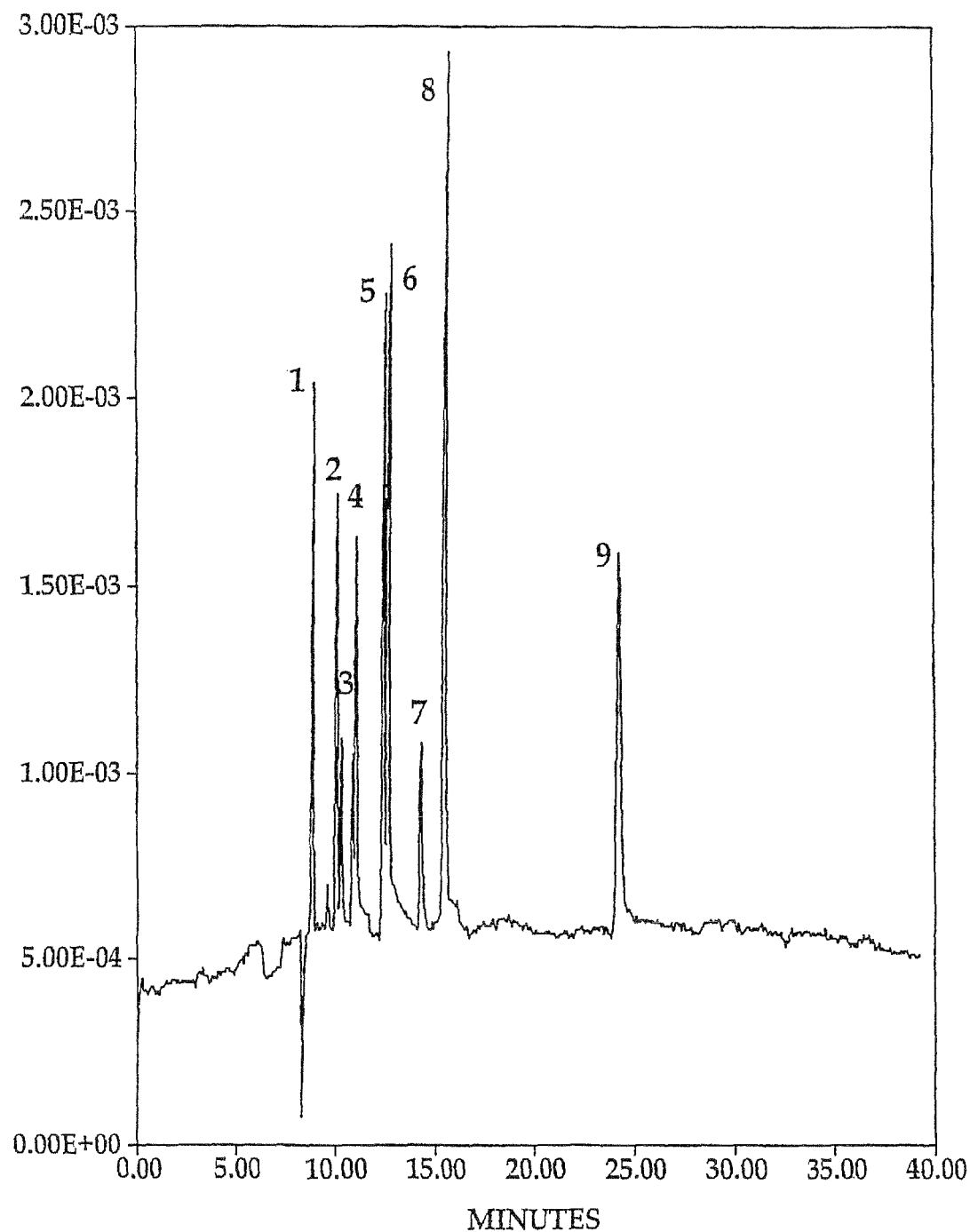
FIG. 5 represents the CEC analysis of a mixture of PAHs on a 50 cm×50 μm ODS sol-gel monolithic column.

The CEC analysis of a mixture of PAHs on a sol-gel ODS monolithic column is shown in FIG. 5. A separation column 50 cm×50 μm inner diameter (46.1 cm effective length) is used. The separation conditions were as follows:

| | |
|---|---|
| Injection | −12 kV for 0.03 min |
| Run | −15 kV, 2.68 μA |
| Mobile phase | 80% acrylonitrile/20% 5 mM Tris-HCl, pH 2.34, DMSO used as the BOF marker |
| Analytes | (1) benzene 4.4053 × 10$^{-6}$ M |
| | (2) naphthalene 2.7087 × 10$^{-6}$ M |
| | (3) impurity |
| | (4) fluorene 1.5433 × 10$^{-6}$ M |
| | (5) phenanthrene 1.5748 × 10$^{-6}$ M |
| | (6) anthracene 9.6850 × 10$^{-7}$ M |
| | (7) fluoranthene 1.1654 × 10$^{-6}$ M |
| | (8) pyrene 1.2283 × 10$^{-6}$ M |
| | (9) benzo[a]pyrene 1.5118 × 10$^{-6}$ M |

The monolithic sol-gel column allowed for the use of a mobile phase containing a higher percentage of acetonitrile (up to 80%) and simultaneously rendered sufficient solute—stationary-phase interactions. The separation efficiencies acquired for naphthalene in the mixture of PAH analytes in this analysis were on the order of 145,800 theoretical plates per meter (73,000 plates/column). Because monolithic columns with overall lengths of up to several meters can be easily prepared by the presented sol-gel technology and that the prepared columns can be operated using commercially available CE instrumentation, new possibilities for generating extremely high efficiencies per column in CEC separations are created.

Figure 6:
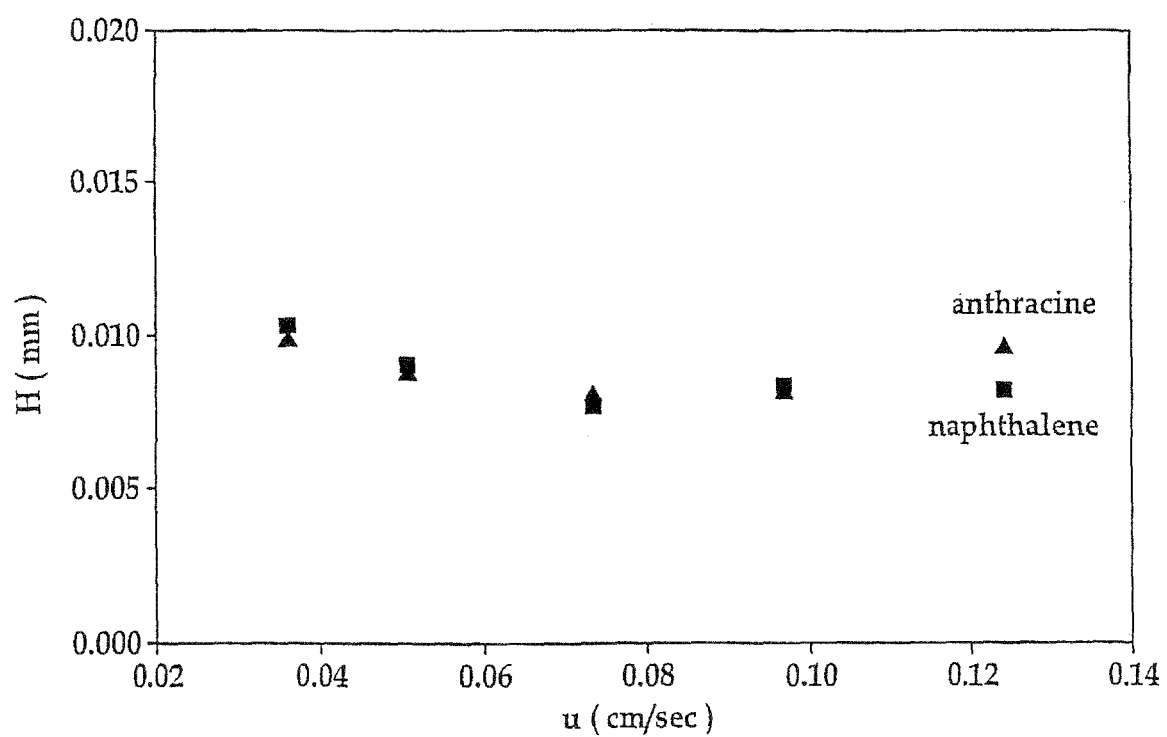
FIG. 6 shows plate height versus flow rate within a sol-gel mediated ODS monolithic capillary.

Van Deemer plots, as depicted in FIG. 6, were constructed through variations in the operating voltages, thereby altering the mobile-phase flow rate through the column and measuring the achieved plate heights corresponding to each operating voltage. The conditions were as follows:

| | |
|---|---|
| Injection | −12 kV for 3 sec |
| Run | −3 to −19 kV |
| Mobile phase | 75% acetonitrile/25% 5 mM Tris-HCl, pH 2.34, DMSO used as the EOF marker |
| Test solutes | (a) naphthalene |
| | (b) anthracene |

For the used test solutes, the Van Deemer plots reveal minimal increases in plate heights as the mobile-phase flow rates are enhanced. The relatively flat right-hand portion of the H vs u curves indicate an efficient mass-transfer process between the mobile phase and the monolithic ODS separation bed.

As can be seen in FIG. 6, the optimum linear velocity for the used sol-gel monolithic ODS column was 0.75 mm/s, which corresponds to applied field strength of −240 V/cm (−12 kV) in the sol-gel monolithic columns. This shows a new possibility for use of longer sol-gel columns that produce higher overall column efficiencies without exceeding the upper voltage limits of commercially available CE instruments. Furthermore, the use of sol-gel technology to prepare these monolithic ODS columns for CEC is further accentuated as increased column lengths can be used because the highly porous structure of the monoliths allows for their rinsing and CEC operation using commercially available CE instrumentation without any additional pressurization capability. There was no need for pressurization of both capillary ends during analysis or for increased pressurization for capillary rinsing prior to analysis. No bubble formation was detected during analysis with the monolithic capillaries when using electric field strengths of up to 300 v/cm. In addition, the highly porous structure of the monolithic capillaries allowed for operation without the need for modification to the commercial CE instrument.

Figure 7:
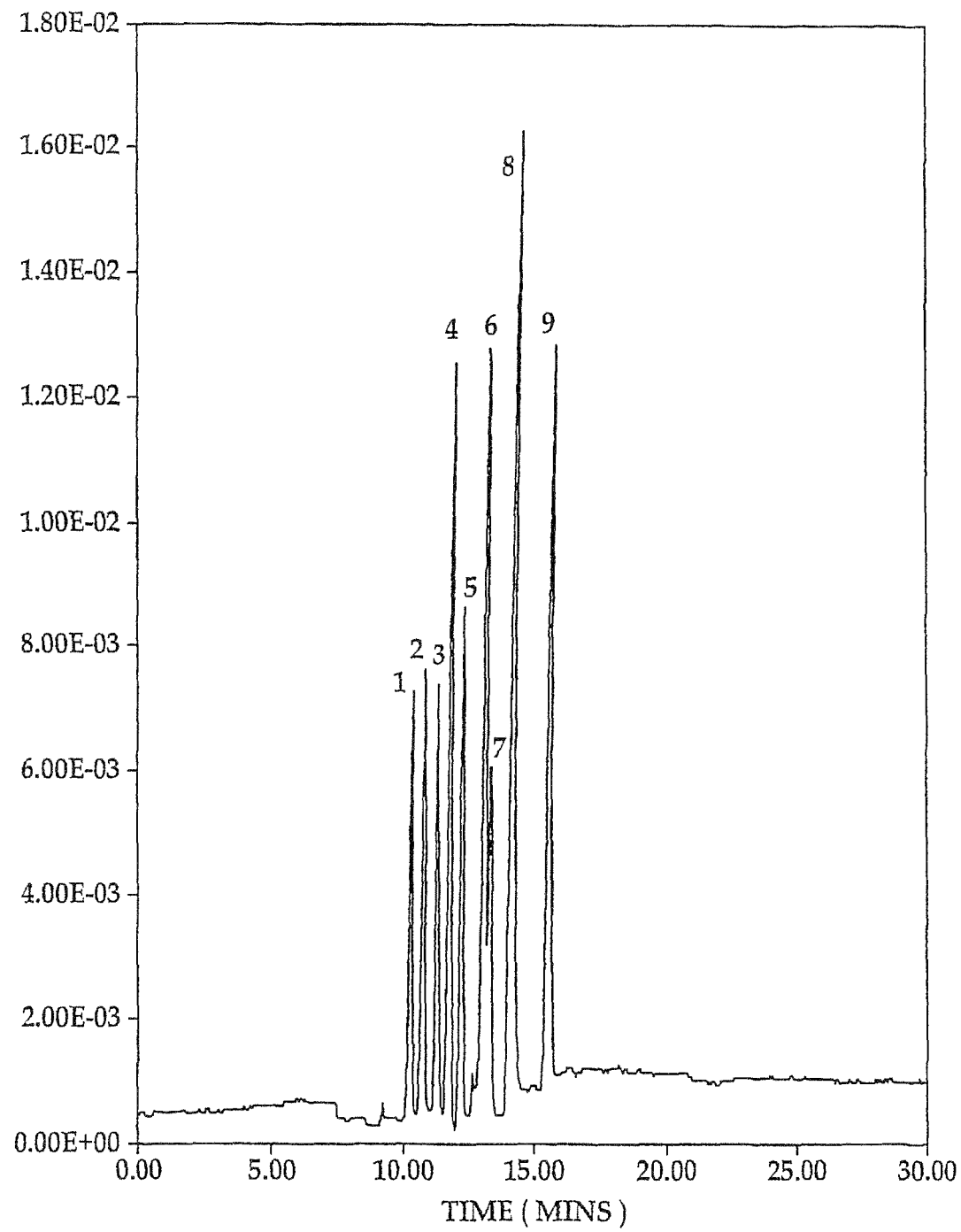
FIG. 7 is a separation analysis of a mixture of benzene derivatives on a sol-gel mediated ODS monolithic column.

A test mixture of benzene derivatives was also used to further evaluate the separation performance of the sol-gel ODS monolithic columns using a mobile phase containing 75% acetonitrile and 25% aqueous 5 mM Tris-HCl at pH of 2.34. Column efficiencies on the order of 163,200 plates/m (81,600 plates/column) were obtained in these analyses as shown in FIG. 7.

Figure 8:
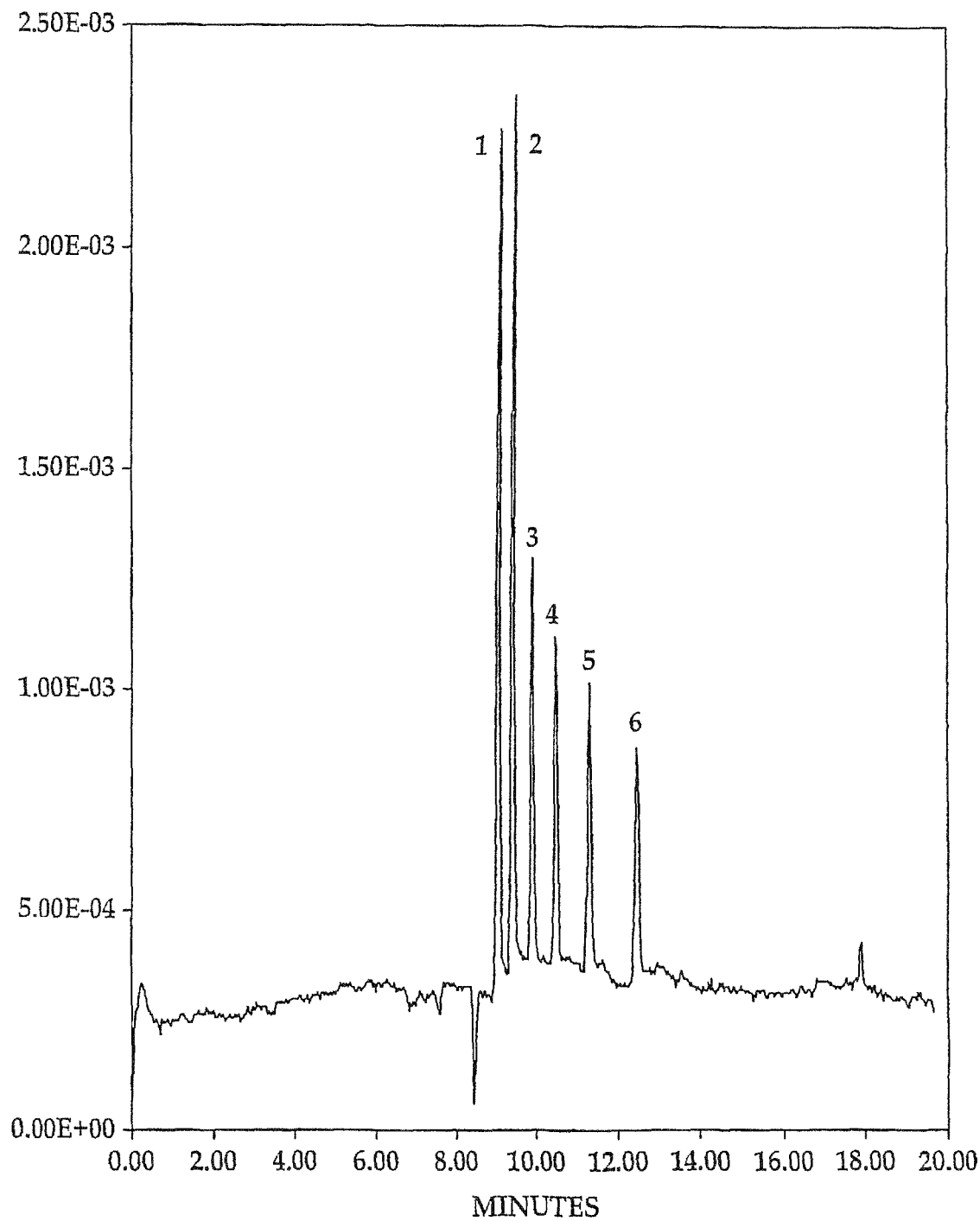
FIG. 8 is a CEC separation of a mixture of aldehydes and ketones on a sol-gel mediated ODS monolithic column.
Figure 9A:
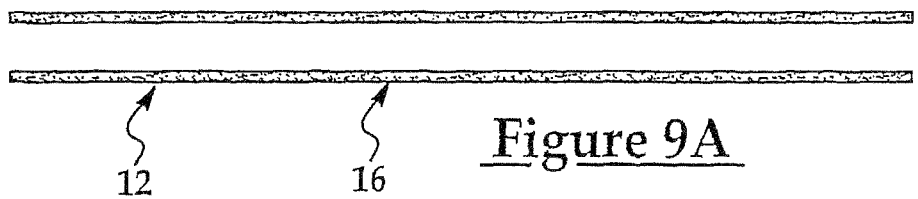
FIG. 9 is a schematic showing the various steps in preparing a monolithic separation column having an additional optical window in the structure.
Figure 9B:
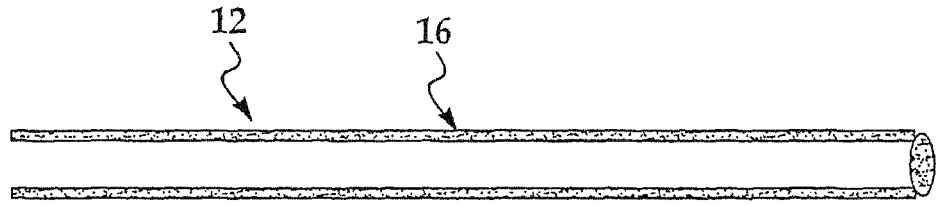
Figure 9C:
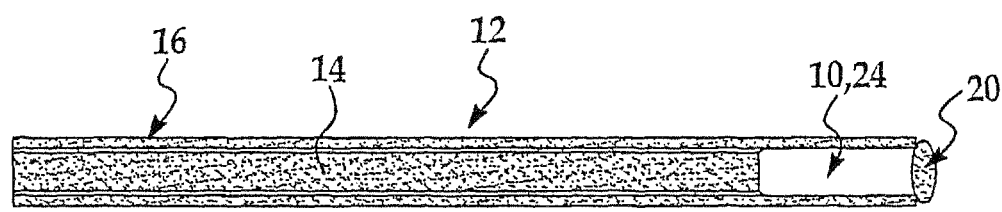
Figure 9D:
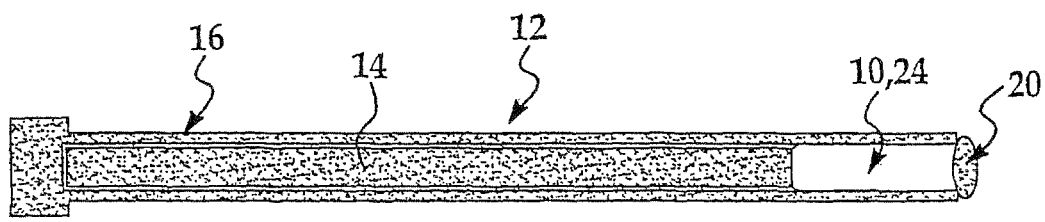
Figure 9E:
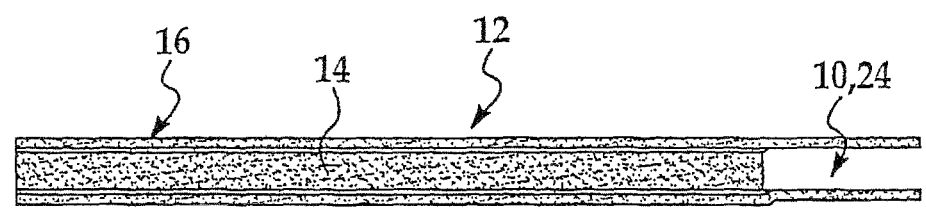
Figure 9F:
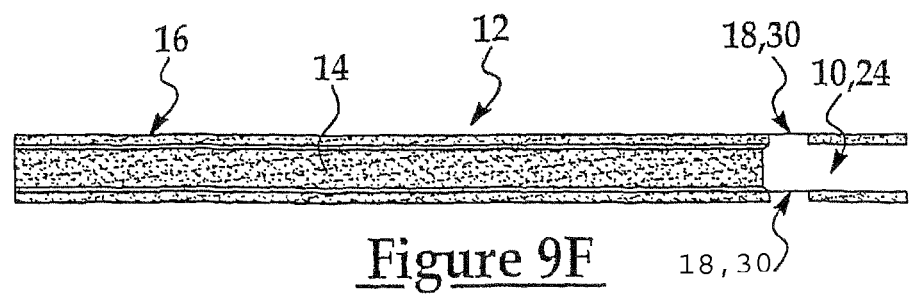

FIG. 8 illustrates an analogous separation of a mixture of aldehydes and ketones obtained on a sol-gel monolithic ODS column. As in the case with the benzene derivatives, this probe mixture contained more closely related analytes. Column efficiencies on the order of 174,600 plates/m (87,300 plates/column) were obtained in these analyses. The conditions here were:

| | |
|---|---|
| Separation column | 50 cm × 50 μm (inner diameter) (46.1 cm of effective length) |
| Injection | −12 kV for 0.03 min |
| | −25 kV 0.5 μA run |
| Mobile phase | 70% acrylonitrile/30% Tris-HCl, pH 2.34 |
| Analytes | (a) benzaldehyde, 1.180 × 10$^{-3}$ M |
| | (b) o-tolualdehyde, 1.9655 × 10$^{-3}$ M |
| | (c) butyrophenone, 3.2680 × 10$^{-4}$ M |
| | (d) valerophenone, 1.5263 × 10$^{-4}$ M |
| | (e) hexaphenone, 3.0618 × 10$^{-4}$ M |
| | (f) heptaphenone, 2.986 × 10$^{-4}$ M. |

Repeatability studies were performed using various analyte mixtures. These experiments were essential to evaluate the consistency in solute retention on the sol-gel monolithic ODS columns. The following table presents the CEC characteristics of sol-gel monolithic columns and experimental data on retention time repeatability for a test mixture of seven aromatic aldehydes and ketones.

| Analyte | Separation Efficiency, N (plates/column) | $t_R$ (min) | Retention factor, k | Separation Factor, α | s | R.S.D. (n = 5) |
|---|---|---|---|---|---|---|
| Benzaldehyde | 89 778 | 9.144 | 0.050 | | 0.027 | 0.295% |
| Tolualdehyde | 91 039 | 9.526 | 0.094 | 0.382 | 0.029 | 0.302% |
| Butyrophenone | 83 867 | 10.048 | 0.154 | 0.522 | 0.025 | 0.248% |
| Valerophenone | 79 353 | 10.678 | 0.227 | 0.630 | 0.016 | 0.154% |
| Hexashenone | 86 027 | 11.550 | 0.327 | 0.872 | 0.022 | 0.194% |
| Heptaphenone | 89 687 | 12.788 | 0.469 | 1.238 | 0.031 | 0.244% |

As depicted in this table, consistent repeatability values are exemplified by the low RSD (0.15-0.30%) values for solute retention times in a series of five consecutive runs.

An additional embodiment of the invention is shown in FIG. 9. This embodiment provides an optical window that allows for the use of a detection device to monitor the eluted analytes after passing through the separation bed. Such an optical window allows for detection or further analysis of samples.

More specifically, the optical window is formed in an area or segment containing gas 10 of the capillary tube, as generally shown at 12, adjacent the sol-gel bed 14. Normally, to provide structural integrity and strength to the tube, an outer coating 16 is provided around the entire outer surface of the tube 12. This outer coating 16 can be in the form of a polymer, metal or other coating as known in the art. In accordance with this embodiment of the present invention, this outer coating 16 is removed from the tube adjacent the sol-gel bed 14, as shown by 18, defining an optical window 30 in the tube in the area of the gas containing area 10.

Generally, the capillary tube 12 itself is optically transparent. However, the outer protective coating 16 interferes with the optical properties thereof. In order to provide the optical window 30, one end of the tube is sealed, as in 20. Under pressure, the sol-gel solution is introduced, thereby compressing the gas within the capillary tube inner gas containing area 10. This forces the formation of a compressed gas space 24, separating an end portion of the bed 14 from the sealed end portion 20. A portion of the outer coating is removed, by burning or by other means known in the art, in the area of the gas containing area 10, thus forming the optical window 30, in the capillary tube. This window may be of any desired size known to those of ordinary skill in the art.

In this embodiment, the separation bed may also be thermally and/or solvent treated as described earlier, and any further necessary pretreatment steps prior to use of the column is considered here as being within the scope of the invention.

A preferred method for forming this window involves the following steps:
(a) selection of an externally coated optically transparent capillary tube, such as one containing a fused-silica inner surface, the coating being any as known to those of ordinary skill in the art, such as polymer, metal or other removable coatings;
(b) sealing of the distal capillary end;
(c) filling the sealed capillary with sol-gel solution, the pressure of the compressed gas in the sealed portion forming a gas pocket in the distal end thereof;
(d) allowing the sol-gel solution inside the capillary to transform into a porous monolithic bed;
(e) sealing the proximal end of the capillary tube to allow thermal conditioning;
(f) removing the seals at both ends of the filled capillary tube to allow for solvent conditioning; and
(g) removing a portion of the outer coating of the capillary tube at the distal end in the region of the former gas pocket to provide a window of any desired length for optical spectrometric analyses.

The incorporation of the optical window allows for additional analyses to be performed on the sample as it exits the separation bed. The choice of spectrometer is within the scope of ordinary skill in the analytical chemistry art, and any known instrument is considered within the scope of the invention. It is also understood that any form of pretreatment of the column may be used including thermal and solvent or both, but the choice of pretreatments is solely a matter of choice.

It may be appreciated by one skilled in the art that additional embodiments may be contemplated, including alternate reagents and tubes used for the outer matrix for the sol-gel filling.

In the foregoing description, certain terms have been used for brevity, clarity and understanding, but no necessary limitations are to be implied therefrom beyond the requirements of the prior art, because such words are used for description purposes herein and are intended to be broadly construed. Moreover, the embodiments of the apparatus and reagents used herein are by way of example, and the scope of the invention is not limited to those in either construction or chemistry.

Having now described the invention, the preferred embodiments thereof and the advantageous new and useful results obtained thereby, along with reasonable chemical equivalents thereof as obvious to those of ordinary skill in the art, these are now set forth in the appended claims.

REFERENCES

Behnke, B.; Bayer, E., *J. Chromatogr. A,* 1994, 680, 93.
Behnke, B.; Grom; E.; Bayer, E., *J. Chromatogr. A,* 1995, 716, 207.
Brinker, C. J.; Scherer, G. W., Sol-gel Science: The Physics and Chemistry of Sol-gel Processing: Academic Press, San Diego, Calif. 1990.
Chong, S.; Wang, D.; Hayes, J. D.; Malik, A. *Anal. Chem.* 1997, 69, 3889.
Colon, L. A.; Fermier, A. M.; Guo, Y.; Reynolds, K. J., *Ninth International Symposium on High Performance Capillary Electrophoresis (HPCE '97),* Anaheim, Calif. 1997.
Cortes, H. J.; Pfeiffer, C. D.; Richter, B. E.; Stevens, T. S., *J. High Resolut. Chromatogr. And Chromatogr. Commun.,* 1987, 10, 446.
Dittmann, M. M.; Rozing, G. P., *J. Chromatogr. A,* 1996, 744, 63.
Dulay, M. T.; Yan, C.; Rakestraw, D. J.; Zare, R. N., *J. Chromatogr. A,* 1996, 725, 361.
Dulay, M. T.; Kulkarni, R. P.; Zare, R. N., *Anal. Chem.,* 1998, 70, 5103.
Ericson, C.; Liao, J.; Nakazato, K.; Hjerten, S., *J. Chromatogr. A* 1997, 767, 33.
Ericson, C.; Hjerten, S., *Anal. Chem.* 1999, 71, 1621.
Fields, S. N., *Anal. Chem.,* 1996, 68, 2709.
Frame, L. A.; Robinson, M. L.; Lough, W. J., *J. Chromatogr. A,* 1998, 798, 243.
Fujimoto, C.; Fujise, Y.; Matsuzawa, E., *Anal. Chem.,* 1995, 716, 107.

Fujimoto, C.; Fujise, Y.; Matsuzawa, E., *Anal. Chem.*, 1996, 68, 2753.
Hayes, J. D.; Malik, A., *J. Chromatogr. B* 1997, 695, 3.
Hayes, J. D., Malik. A., manuscript in progress.
Hileman, F. D.; Sievers, R. E.; Hess, G. G.; Ross, W. D., *Anal. Chem.*, 1973, 45, 1126.
Hjerten, S.; Liao, J. L; Zhang, R., *J. Chromatogr.*, 1989, 473, 273.
Hjerten, S.; Li, Y. M.; Liao, J. L.; Mohammad, J.; Nakazato, K.; Pettersson, G., *Nature*, 1992, 356, 810.
Ishizuka, N.; Minakuchi, H.; Nakanishi, K.; Soga, N.; Tanaka, N., *J. Chromatogr. A*, 1998, 797, 131.
Jorgenson, J. W.; Lucas, K. D., *J. Chromatogr. A*, 1981, 218, 209.
Knox, J. H.; Grant, I. H., *Chromatographia*, 1987, 24, 135.
Li, Y. M.; Liao, J. L.; Nakazato, K.; Mohammad, J.; Terenius, L.; Hjerten, S., *Anal. Biochem.* 1994, 223, 153.
Ludtke, S.; Adam T.; Unger, K. K., *J. Chromatogr. A*, 1997, 786, 229.
Malik, A.; Chong, S. in Pawliszyn, J. (ed.), "Applications of Solid Phase Microextraction," Royal Society of Chemistry, 1999, United Kingdom, Ch. 6, pp. 73-91.
Minakuchi, H.; Nakanishi, K.; Saga, N.; Ishizuka, N.; Tanaka, N., *Anal. Chem.*, 1996, 68, 3498.
Minakuchi, H.; Nakanishi, K.; Soga, N.; Ishizuka, N.; Tanaka, N., *J. Chromatogr. A*. 1997, 8, 547.
Minakuchi, H.; Nakanishi, K.; Soga, N.; Ishizuka, N.; Tanaka, N., *J. Chromatogr. A*, 1998, 797, 121.
Moffatt, F.; Cooper, P. A.; Jessop, K. M., *Anal. Chem.*, 1999, 71, 1119.
Nakanishi, K. K; Minalcuchi, H.; Soga, N.; Tanaka, N., *J. Sol-gel Sci. and Tech.* 1997, 762, 135.
Palm, A.; Novotny, M. V., *Anal. Chem.* 1997, 69, 4499.
Peters, E. C.; Petro, M.; Svec, F.; Frechet, J. M. J., *Anal. Chem.* 1997, 69, 3646.
Peters, E. C.; Petro, M.; Svec, F.; Frechet, J. M. J., *Anal. Chem.* 1998, 70, 2288.
Pietrzyk, D. J. in *Packings and Stationary Phases in Chromatographic Techniques*; Unger, K. K., Ed.; Vol. 47; Marcel Dekker: New York 1990; Chapter 10.
Pretorius, V; Hopkins, B. J.; Schieke, J. D., *J. Chromatogr. A*, 1974, 99:23.
Seifer, R. M.; Kraak, J. C.; Th. Kok, W.; Poppe, H., *J. Chromatogr. A*, 1998, 808, 71.
Smith, N. W.; Evans, M. C., *Chromatographia* 1994, 38, 649.
Svec, F.; Frechet, J. M. J., *Anal. Chem.* 1992, 64, 820.
Svec, F.; Frechet, J. M. J., *J. Chromatogr. A* 1995, 702, 89.
Tang; Q.; Wu, N.; Lee, M. L., *J. Microcol. September,* 1999, 11, 550.
Tsuda, T., *Anal. Chem.*, 1987, 59, 521.
Van den Bosch, S. E.; Heemstra, S.; Kraak, J. C.; Poppe, H., *J. Chromatogr. A*, 1996, 755, 165.
Wang, Q. C.; Svec, F.; Frechet, J. M. J., *Anal. Chem.* 1993, 65, 2243.
Wang, D.; Chong, S.; Malik, A. *Anal. Chem.* 1997, 69, 4566.
Wei, W.; Luo, G. A.; Hua, G. Y.; Yan, C., *J. Chromatogr. A*, 1998, 817, 65.
Xin, B.; Lee, M. L., *Electrophoresis*, 1999, 20, 67.
Yan, C.; Dadoo, R.; Zhao, H.; Zare, R. N.; Rakestraw, D. J., *Anal. Chem.*, 1995, 67, 2026.
Yang, C.; El Rassi, Z. *Electrophoresis* 1998, 19, 2278.
Yang, C.; El Rassi, Z., *J. Jig. Chromatogr.* 1995, 18, 3373.
Zhang, M.; El Rassi, Z., *Electrophoresis*, 1998, 19, 2068.
Zhang, M.; El Rassi, Z., *Electrophoresis*, 1999, 20, 31.
Zhang, M.; Yang, C.; El Rassi, Z., *Anal. Chem.*, 1999, 71, 3277.
Zimina, T. M.; Smith, R. M.; Meyers, P., *J. Chromatogr. A,* 1997, 758, 191.

We claim:

1. A monolithic sol-gel column produced by forming a monolithic separation bed from a sol-gel solution in a single step, wherein said monolithic sol-gel column comprises an optically transparent capillary tube having an inner surface; and a porous matrix of substantially homogeneous composition and being free of chromatographic particles, wherein said porous matrix is formed in situ inside said capillary tube with a gas pocket at a sealed distal end of said capillary tube that prevents said porous matrix from contacting said distal end, and wherein said porous matrix is chemically bonded to the inner surface of said capillary tube; and wherein said distal end of said capillary tube that has not been contacted by said porous matrix remains optically transparent, and wherein said porous matrix comprises:

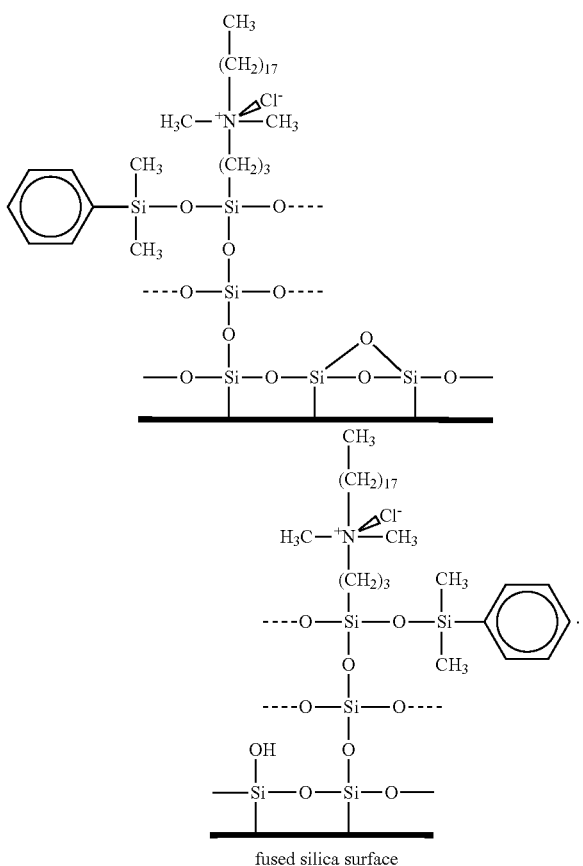

2. The monolithic sol-gel column according to claim 1, wherein an outer coating is provided around the surface of said capillary tube.

3. The monolithic sol-gel column according to claim 1, wherein said capillary tube is a fused silica capillary tube.

4. The monolithic sol-gel column according to claim 1, wherein said sealed distal end of said capillary tube is unsealed following the chemical bonding of said porous matrix to the inner surface of said capillary tube.

5. A sol-gel column produced by the process of:
   a) selecting an optically transparent capillary tube having a protective outer coating suitable for forming a monolithic sol-gel column;
   b) sealing one end of said tube;

c) adding a sol-gel solution to an open end of said tube under pressure to form a sol-gel filled column with a gas pocket at the sealed end of said tube, wherein said gas pocket prevents said sol-gel solution from contacting the sealed end of said tube;

d) solidifying said sol-gel solution to form a porous matrix of substantially homogeneous composition and being free of chromatographic particles, wherein said porous matrix is chemically bonded to the inner surface of said capillary tube; and e) removing a portion of said protective coating in the area of said gas pocket region adjacent to said filled portion of said tube to thereby form an optical window;

wherein said porous matrix comprises:

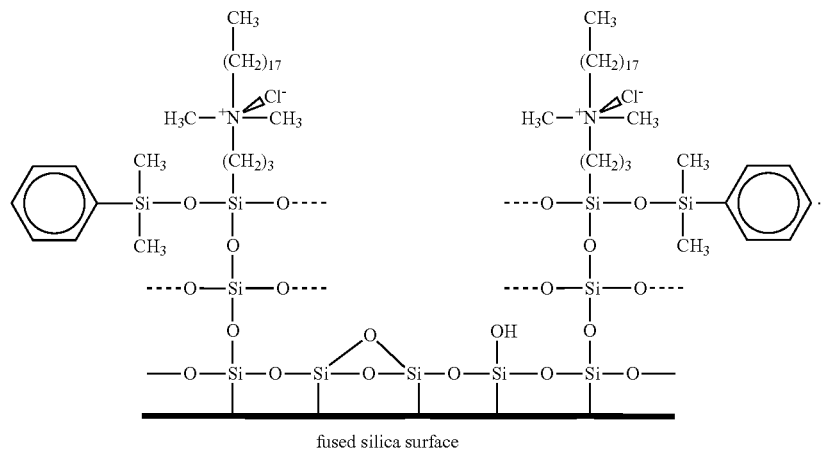

6. The sol-gel column according to claim 5, wherein said sealed end of said capillary tube is unsealed following the chemical bonding of said porous matrix to the inner surface of said capillary tube.

7. The sol-gel column according to claim 5, wherein said capillary tube is a fused silica capillary tube.

\* \* \* \* \*

UNITED STATES PATENT AND TRADEMARK OFFICE
CERTIFICATE OF CORRECTION

PATENT NO. : 8,597,508 B2  Page 1 of 1
APPLICATION NO. : 13/102651
DATED : December 3, 2013
INVENTOR(S) : Abdul Malik et al.

It is certified that error appears in the above-identified patent and that said Letters Patent is hereby corrected as shown below:

In the Specifications

Column 2,
Line 15, "flits of a" should read --frits of a--
Line 17, "flits remains" should read --frits remains--
Line 18, "flits must" should read --frits must--
Line 21, "flits must" should read --frits must--
Line 61, "columns-containing" should read --columns containing--

Column 8,

Line 55, " 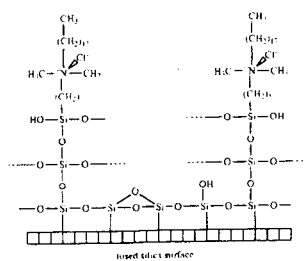 " should read -- 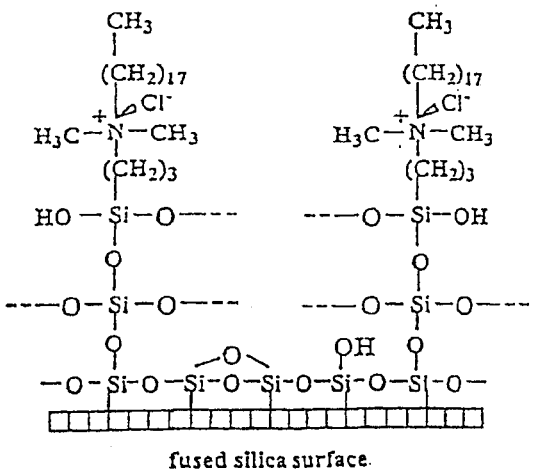 --

Column 11,
Line 42, "as the BOF" should read --as the EOF--

Signed and Sealed this
Fifteenth Day of April, 2014

Michelle K. Lee
*Deputy Director of the United States Patent and Trademark Office*